US011057741B2

(12) United States Patent
Hunter

(10) Patent No.: US 11,057,741 B2
(45) Date of Patent: Jul. 6, 2021

(54) PERSONAL MONITORING SYSTEM

(71) Applicant: Jack C. Hunter, Boone, NC (US)

(72) Inventor: Jack C. Hunter, Boone, NC (US)

(*) Notice: Subject to any disclaimer, the term of this patent is extended or adjusted under 35 U.S.C. 154(b) by 0 days.

(21) Appl. No.: 16/717,688

(22) Filed: Dec. 17, 2019

(65) Prior Publication Data
US 2020/0196105 A1 Jun. 18, 2020

Related U.S. Application Data

(60) Provisional application No. 62/780,652, filed on Dec. 17, 2018.

(51) Int. Cl.
*H04W 4/029* (2018.01)
*H04W 4/38* (2018.01)
*H04W 4/02* (2018.01)
*H04W 4/021* (2018.01)

(52) U.S. Cl.
CPC .......... *H04W 4/029* (2018.02); *H04W 4/021* (2013.01); *H04W 4/027* (2013.01); *H04W 4/38* (2018.02)

(58) Field of Classification Search
CPC ....... H04W 4/029; H04W 4/38; H04W 4/021; H04W 4/027
USPC ....................................................... 455/456.1
See application file for complete search history.

(56) References Cited

U.S. PATENT DOCUMENTS

| 5,731,757 | A | * | 3/1998 | Layson, Jr. | .......... | G08B 21/028 340/5.61 |
| 6,100,806 | A | | 8/2000 | Gaukel | | |
| 6,774,797 | B2 | * | 8/2004 | Freathy | .......... | G07C 9/28 340/573.1 |
| 6,952,574 | B2 | * | 10/2005 | Tealdi | .......... | H04W 60/00 455/404.2 |
| 7,647,196 | B2 | | 1/2010 | Kahn et al. | | |
| 7,955,268 | B2 | | 6/2011 | Huelskamp | | |
| 8,086,250 | B2 | * | 12/2011 | Janetis | .......... | G01S 19/34 455/404.1 |
| 8,558,690 | B2 | | 10/2013 | Kleve et al. | | |
| 9,275,093 | B2 | | 3/2016 | Pandey et al. | | |
| 9,788,354 | B2 | | 10/2017 | Miller et al. | | |

(Continued)

OTHER PUBLICATIONS

International Searching Authority, International Search Report and Written Opinion, issued for International Application No. PCT/US2019/066902, dated Feb. 25, 2020 (12 pages).

*Primary Examiner* — William Nealon
(74) *Attorney, Agent, or Firm* — Polsinelli PC

(57) ABSTRACT

Systems and methods for improved personal monitoring systems and devices include the provision of sensor data from a personal monitoring device to a server system. The sensor device is provided to the server system at a first rate and subsequently analyzed by the server system. If the server system determines that a particular condition is met based on the sensor data the server system transmits a reconfiguration message to the personal monitoring device that causes the personal monitoring device to automatically begin providing data at a second rate. Among other things, the condition resulting in generation and transmission of the reconfiguration message may include a location-based condition (e.g., crossing a geographic boundary), a change in an environmental condition (e.g., temperature or air quality), or a movement-based condition (e.g., an acceleration indicative of a fall or collision).

20 Claims, 13 Drawing Sheets

(56) References Cited

U.S. PATENT DOCUMENTS

| | | | |
|---|---|---|---|
| 2005/0068169 A1* | 3/2005 | Copley | G08B 21/0283 |
| | | | 340/539.13 |
| 2007/0072620 A1* | 3/2007 | Levitan | H04W 4/029 |
| | | | 455/456.1 |
| 2007/0229350 A1* | 10/2007 | Scalisi | G06F 21/83 |
| | | | 342/350 |
| 2008/0174422 A1* | 7/2008 | Freathy | H04W 4/029 |
| | | | 340/539.13 |
| 2012/0206296 A1* | 8/2012 | Wan | H02K 7/1853 |
| | | | 342/357.31 |
| 2016/0058390 A1 | 3/2016 | Dyell et al. | |
| 2017/0206498 A1* | 7/2017 | Hamm | G06Q 10/087 |

* cited by examiner

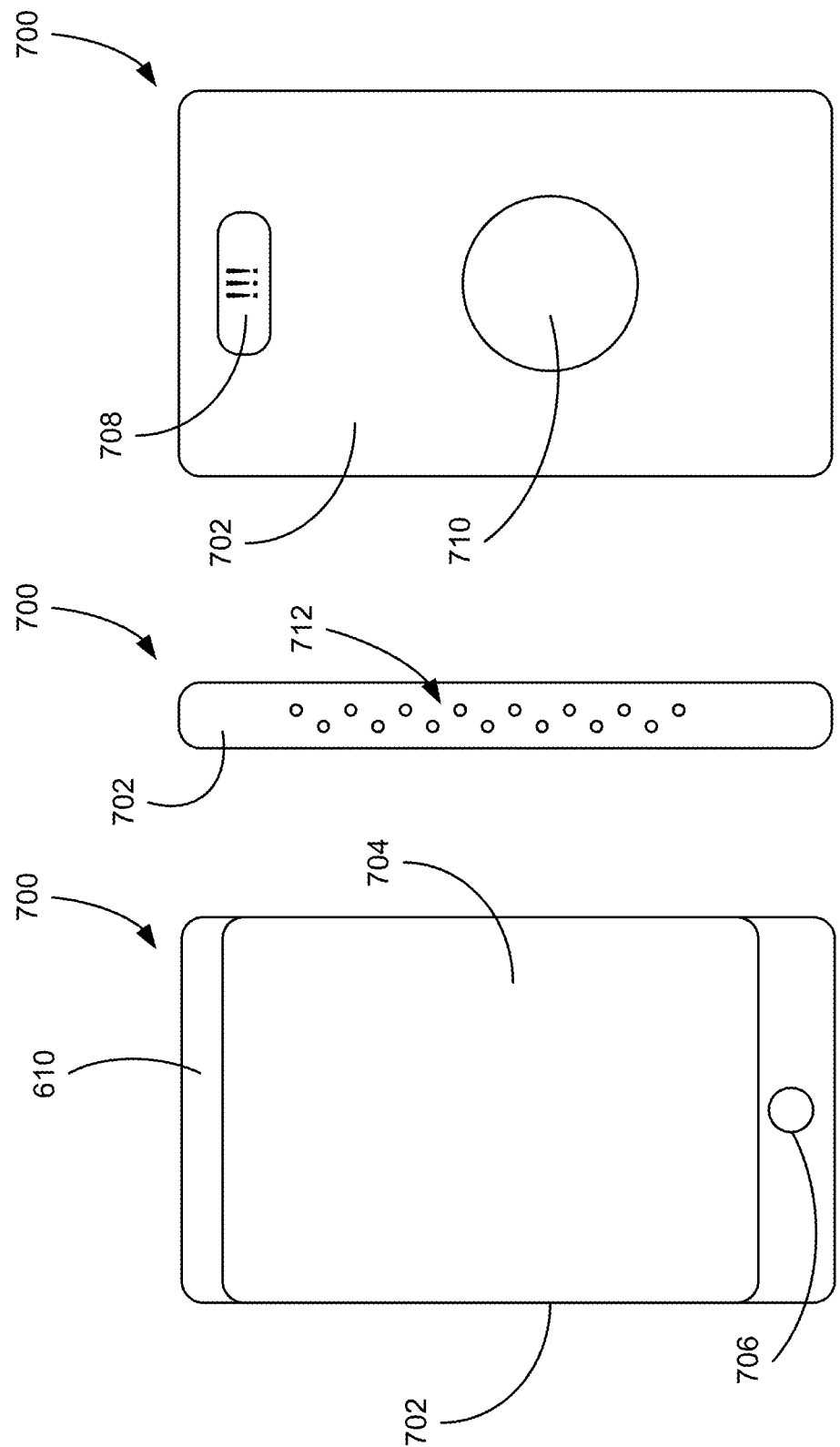

PERSONAL MONITORING SYSTEM

CROSS-REFERENCE TO RELATED APPLICATION

This application is related to and claims priority under 35 U.S.C. § 119(e) from U.S. Patent Application No. 62/780,652, filed Dec. 17, 2018, entitled "Personal Monitoring System", the entire contents of which is incorporated herein by reference for all purposes.

TECHNICAL FIELD

Aspects of the present disclosure involve systems, methods, and devices for facilitating personal monitoring. Among other things, implementations of the present disclosure include personal monitoring devices and associated computing systems for communicating with the personal monitoring devices and receiving and processing data from the personal monitoring devices.

BACKGROUND

Personal tracking systems generally enable a remote user to determine the location or similar details regarding a user of a personal tracking device. Such systems have many applications including general monitoring of children, the disabled, the elderly, or other similar individuals and identification and reporting of emergency situations. Among other things, such systems may provide the monitored individual with a greater degree of autonomy (e.g., versus being in a constantly and more directly monitored environment, such as a nursing home) while simultaneously providing the caretaker with the peace of mind that any potentially hazardous situations that may arise will be quickly identified and addressed.

Conventional tracking and monitoring systems often require a tradeoff between functionality, device format, and battery life. So, for example, small, energy efficient monitoring devices are often have limited functionality, such as the amount and type of data they provide. Conversely, more sophisticated and feature-heavy monitoring devices often require a larger device or a device requiring more power. In light of the foregoing, there is a need for a personal monitoring system having sophisticated features and functionality without significant impact to the form or life of the personal monitoring device.

It is with the foregoing in mind, among other things, that aspects of the present disclosure were conceived and developed.

SUMMARY

In one aspect of the present disclosure, a method of tracking devices is provided. The method includes receiving sensor data at a first computing device from a second computing device at a first rate. The first computing device then determines whether the sensor data indicates a reconfiguration condition. In response to determining that the sensor data indicates a reconfiguration condition, the first computing device generates and transmits a reconfiguration message to the second computing device, the reconfiguration message configured to automatically cause the second computing device to begin providing sensor data at a second rate different than the first rate.

In another aspect of the present disclosure, another method of tracking computing devices is provided. The method includes periodically transmitting sensor data at a first rate from a first computing device to a second computing device. The method further includes receiving a reconfiguration message from the second computing device at the first computing device in response to the sensor data. In response to the reconfiguration message, the first computing device begins periodically transmitting sensor data at a second rate different than the first rate.

In yet another aspect of the present disclosure, a system for tracking computing devices is provided. The system includes one or more hardware processors configured by machine-readable instruction to receive sensor data from a computing device at a first rate. The instructions further cause the one or more hardware processors to determine that the sensor data indicates a reconfiguration condition. The instructions further cause the one or more hardware processors to generate and transmit a reconfiguration message to the computing device, the reconfiguration message configured to automatically cause the computing device to begin providing sensor data at a second rate different than the first rate.

BRIEF DESCRIPTION OF THE DRAWINGS

The foregoing and other objects, features, and advantages of the present disclosure set forth herein will be apparent from the following description of particular implementations of those inventive concepts, as illustrated in the accompanying drawings. It should be noted that the drawings are not necessarily to scale; however the emphasis instead is being placed on illustrating the principles of the inventive concepts. Also, in the drawings the like reference characters may refer to the same parts or similar throughout the different views. It is intended that the implementations disclosed herein are to be considered illustrative rather than limiting.

FIGS. 7A-7C are front, side, and rear views, respectively, of a fourth example personal monitoring device according to the present disclosure;

DETAILED DESCRIPTION

The present disclosure is directed to methods, systems, and devices for personal monitoring. Among other things, implementations of the present disclosure include a personal monitoring device in communication with a server system that receives and processes sensor data (such as, but not limited to, location and acceleration data) from the personal monitoring device. The server system is also accessible by a remote computing device (such as a smartphone, tablet, or personal computer) such that a user of the remote computing device can, among other things, access and evaluate the sensor data provided by the personal monitoring device or be alerted when the sensor data provided by the personal monitoring device indicates the occurrence of certain events.

Although a wide range of example applications are discussed herein, in one specific example, the personal monitoring device may be provided to a child such that the personal monitoring device periodically provides the location of the child to the server system. A parent operating the remote computing device can subsequently access the location data to determine the location of their child. In such implementations, the server system may also be configured to transmit an alert or other notification to the remote computing device in the event the child exits a defined area, is within proximity of a particular location, or otherwise meets a location-related criteria. In another example implementation, the personal monitoring device may be used by an elderly person and configured to transmit acceleration and location data when an accelerometer of the personal monitoring device measures acceleration above a threshold indicative of a fall. In such implementations, the personal monitoring device and server system may automatically initiate a call to an emergency contact or emergency service, automatically transmit a notification to the remote computing device, or take other similar steps to initiate assistance for the user of the personal monitoring device.

In implementations of the present disclosure, the personal monitoring device is generally configured to have relatively simple and limited functionality. For example, while the personal monitoring device may measure and store sensor data, processing of the sensor data to determine whether monitoring conditions (e.g., leaving a geographic area, a fall, etc.) have been met is generally handled by the server system. Moreover, personal monitoring devices in accordance with the present disclosure may also include functionality to modify sensor sampling rates or to operate in low-power modes in order to preserve battery charge.

The foregoing aspects of the present disclosure, among others, are now provided in further detail with reference to the figures.

A. System Overview

Figure 1:
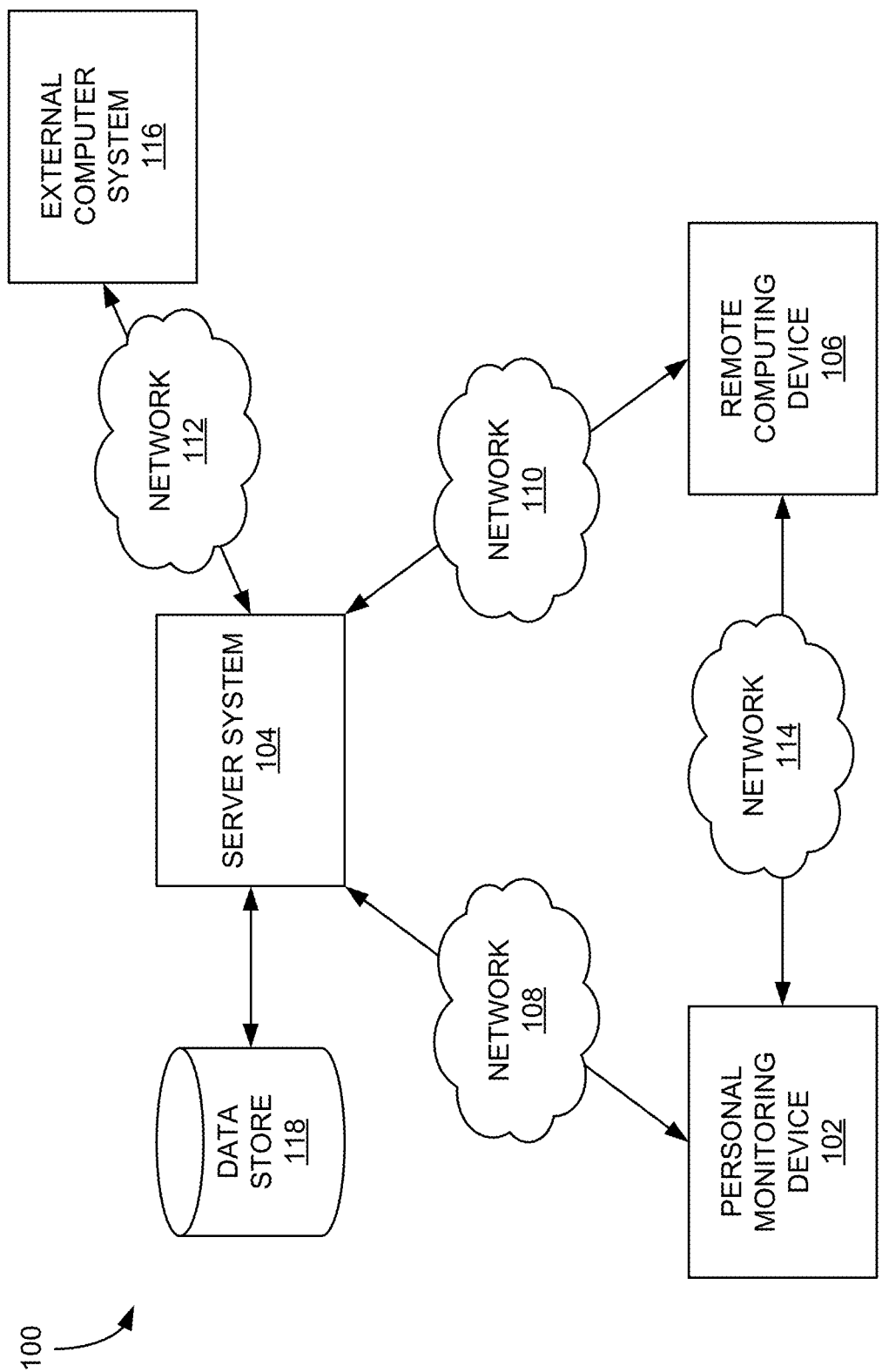
FIG. 1 is a system diagram illustrating an example operational environment for implementations of the present disclosure including a personal monitoring device and a server system.

FIG. 1 is a block diagram illustrating a network environment 100 for implementing aspects of the present disclosure. As shown in FIG. 1, the network environment 100 includes a personal monitoring device 102 in communication with a server system 104 over a network 108. The network environment 100 further includes a remote device 106 in communication with the server system 104 over a network 110, and an external computer system 116 in communication with the server system 104 over a network 112. The server system 104 may also include or be in communication with one or more data sources, such as data store 118.

For simplicity, the network environment 100 of FIG. 1 is illustrated as including a single instance of each environmental element. However, it should be appreciated that the network environment 100 is intended merely as a basic example to illustrate aspects of the present disclosure. More generally, network environments in accordance with the present disclosure may include one or more of any of the network elements illustrated in FIG. 1. So, for example, implementations of the present disclosure may connect any number of personal monitoring devices 102 to any number of remote computing devices 106 via any number of server systems 104. Moreover, while illustrated as individual blocks, each element may instead be distributed over multiple systems or devices. For example, each of the server system 104 and the data store 118 may be distributed across multiple computing devices or systems, such as in a cloud computing environment.

Personal monitoring device 102 is generally a wearable or otherwise portable computing device including one or more sensors including, for example and without limitation, location-based sensors, movement-based sensors, environmental sensors, and the like. During operation, the personal monitoring device 102 collects data from its onboard sensors and transmits the sensor data to the server system 104. In certain implementations, the personal monitoring device 102 may be a device intended to be worn or carried by a child, elderly person, or other individual who, due to age, mental state, or other condition, may require periodic or constant monitoring.

The server system 104 in turn processes and stores the data, such as in data store 118. As described herein in further detail, processing the sensor data received from the personal monitoring device 102 includes may include a wide range of functions. Among other things, processing the sensor data may include determining whether the personal monitoring device 102 is within or outside of particular location or environment or whether movement data from the personal monitoring device 102 indicates that a user may have fallen, been struck by a vehicle, etc. In response, the server system 104 may, among other things and without limitation, transmit reconfiguration messages to the personal monitoring device 102, transmit alerts or notifications to the remote computing device 106, or perform similar responsive actions.

The server system 104 may also provide access to the collected sensor data regardless of whether a reportable event has occurred. For example, a parent, guardian, or similar user may access data collected by the server system using the remote computing device 106. The remote computing device 106 may be a smart phone, laptop, tablet, desktop computer, or any other similar computing device and may access the data on the server system 104 using an application, program, web browser, etc. executed on the remote computing device 106. In some implementations, the server system 104 may generate and provide graphs, tables, maps, or other representations of the collected sensor data for presentation on the remote computing device 106.

In addition to presenting collected sensor data, the remote computing device 106 may be used to communicate with the server system 104 to configure or otherwise establish rules and corresponding actions to be taken by the server system 104. Each rule may generally include one or more conditions related to location, environment, or other parameter measurable by the personal monitoring device 102. When the one or more conditions are met, the server system 104 may then execute an action such as, but not limited to, generating and transmitting an alert or notification to the personal monitoring device 102 and/or the remote computing device 106, initiating a call or communication link between the personal monitoring device 102 and/or the remote computing device 106, transmitting an alert or notification to a third-party (e.g., a caretaker, teacher, healthcare professional, or similar individual), transmitting a message to the personal monitoring device 102 to modify operation of the personal monitoring device 102, or other similar actions. Specific but non-limiting examples of such functionality are provided herein.

To facilitate the various functions provided by the server system 104, the server system 104 may access or otherwise communicate with one or more external computer systems 116. Such computing systems may include, without limitation, mapping/geolocations systems (e.g., for accessing map information over which collected sensor data may be overlaid), weather data systems (e.g., to access various air quality metrics), payment systems, communication systems, social media systems, ride sharing systems, etc.

As illustrated in FIG. 1, each of the personal monitoring device 102, the remote computing device 106, and the external computer system 116 is communicatively coupled to the server system 104 by a respective network 108, 110, 112. Although illustrated as separate networks, the networks 108, 110, and 112 may instead correspond to a single, broader network, such as the Internet. More generally, the networks 108, 110, and 112 represent any suitable communication connection to the server system 104. Similarly, each network 108, 110, 112 may use any suitable communication medium or protocol and, in particular, may be implemented using wired, wireless, or a combination of wired and wireless connections.

The personal monitoring device 102 is also illustrated as being connected to the remote computing device 106 by a network 114. Similar to the networks 108-112, the network 114 may be any suitable network using any suitable communication protocol. Nevertheless, in at least certain implementations, the network 114 may be a cellular network that enables cellular communication between the personal monitoring device 102 and the remote computing device 106.

In certain implementations, any of the personal monitoring device 102, the server system 104, and the remote computing device 106 may store and maintain information and data for a particular user of the personal monitoring device 102 over time. Such data may include data collected from the personal monitoring device 102, but also additional personal and health information provided by users of the personal monitoring device 102, users of the remote computing device 106 or other individuals, such as doctors or similar medical professionals. As such data is collected it may be analyzed to generate various statistics and trends for a given user. For example and without limitation, such statistics may include the amount of time a user has spent in particular environmental conditions and the total exposure of the user to various pollutants/particles over time. Based on such information, alerts or warnings may be generated and transmitted to the user of the personal monitoring device 102 or individuals associated with the user.

B. Example Personal Monitoring Device

Figure 2:
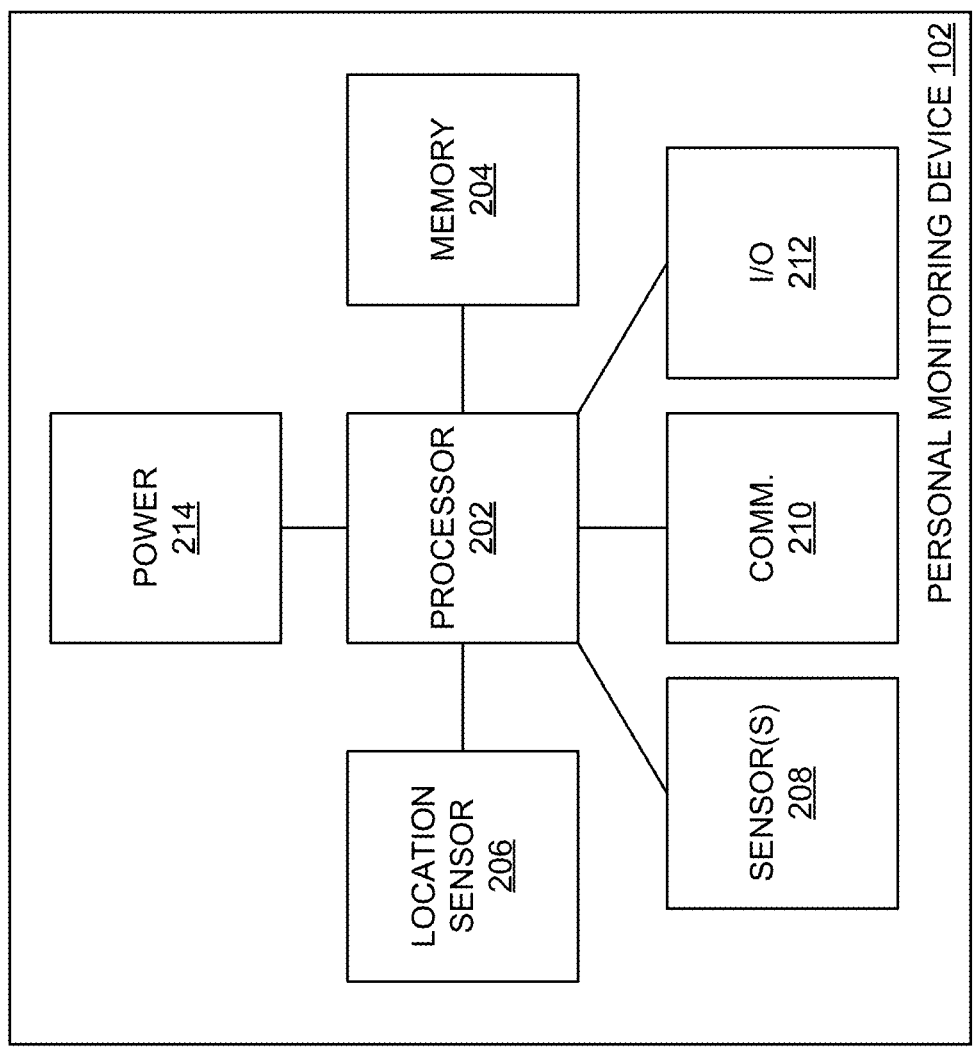
FIG. 2 is a block diagram illustrating an example implementation of the personal monitoring device of FIG. 1.

FIG. 2 is a block diagram illustrating an example implementation of the personal monitoring device 102. As illustrated, the personal monitoring device 102 includes one or more processors 202, one or more memories 204, and other similar computing components. During operation, the processor 202 executes instructions stored in the memory 204 to control the other components and to process data, as described below in further detail.

The personal monitoring device 102 includes a location sensor 206 for measuring a position of the personal monitoring device 102 and, by extension, a location of a user of the personal monitoring device 102. In one implementation, the location sensor 206 may be a global positioning system (GPS) unit configured to periodically measure the current position of the personal monitoring device 102. The location sensor 206 may be further configured to provide additional information based on the collected position information. For example and without limitation, such information may include speed information (e.g., current speed, average speed) and distance information (e.g., total distance travelled, distance travelled from a waypoint or similar location).

The personal monitoring device 102 may also include one or more other sensors, collectively indicated in FIG. 2 as a sensor(s) 208, for measuring other conditions associated with the personal monitoring device 102. For example and without limitation, the sensor 208 may be configured to measure conditions of the environment (e.g., temperature, air quality, etc.) within which the personal monitoring device 102 is disposed or physical changes to the personal monitoring device 102 (e.g., movement, acceleration, etc.).

In one specific implementation, the sensor 208 may include one or more sensors directed to measuring air quality. Such implementations may be useful to monitor individuals with various health-related conditions that may be triggered or exacerbated by poor air quality including, for example and without limitation, chronic obstructive pulmonary disease (COPD), a suppressed or otherwise compromised immune system, air-borne allergies, asthma, and the like. Example air quality-related sensors that may be used in implementations of the present disclosure include, without limitation, one or more of a PM2.5 (or other particulate) sensor, a temperature sensor, a pressure sensor, a humidity sensor, and any of a number of chemical sensors. Examples of such chemical sensors include, without limitation, sensors for measuring one or more of volatile organic compounds (VOCs), carbon monoxide (CO), nitrogen oxides (NOx), hydrogen sulfide ($H_2S$), and other chemicals that may be indicative of air quality.

In addition to or instead of air quality-related sensors, the sensor 208 may also include other environmental sensors, such as light sensors/photodetectors and/or one or more sensors adapted to measure movement of the personal monitoring device. Such sensors may include, for example, one or more of an accelerometer and a gyroscope. The movement sensors may be configured to generally track and facilitate recording movement of the personal monitoring device 102 and, as a result, may be used to interpret and analyze movement of the user of the personal monitoring device 102.

The personal monitoring device 102 may also include at least one communications unit 210 to facilitate communication between the personal monitoring device 102 and one or more external devices. While the communications unit 210 generally facilitates communication with the server system 104, the communications unit 210 may also facilitate communication with various other external devices including, without limitation, one or more of another instance of the personal monitoring device; one or more wearable sensors; a laptop, tablet, smart phone or other computing device (including the remote computing device 106); a cellular communications system; or any other device that supports such communication. The communications unit 210 may be configured to communicate and support one or more communication protocols. Such protocols may include, without limitation, one or more of Bluetooth® (including Bluetooth® Low-Energy), Wi-Fi, cellular (e.g., 3G or 4G cellular), near-field communication (NFC), or any other similar communication protocols. It should also be noted that while described primarily herein as being capable of wireless communication, the communications unit 210 may further include one or more ports to support wired communication, such as a universal serial bus (USB) connection.

The personal monitoring device 102 may further include one or more input/output (I/O) units 212 to facilitate interaction with a user of the personal monitoring device 102. With respect to inputs received from the user, such inputs are processed by the processor 202 and used to initiate execution of instructions stored in the memory 204 or to otherwise control operation of the personal monitoring device 102. In one example implementation, the I/O unit 212 may include physical buttons and/or "virtual" buttons (e.g., buttons or icons presented on a display of the personal monitoring device 102). In the latter case, the I/O unit 212 may include, at least in part, a touchscreen and, as a result, may be at least partially integrated with aspects of an output or display device (not shown) of the personal monitoring device 102. In other implementations, the input devices may additionally or alternatively include various other input mechanisms including, without limitation, one or more of a microphone, a switch, a rotary dial, or any other similar input mechanism.

The I/O unit 212 may include a display configured to display information to a user of the personal monitoring device 102. In certain implementations, the display may include a liquid crystal display (LCD) or light-emitting diode (LED) screen that may be controlled or otherwise receive instructions from the processor 202 to display different information and data. Such data and information may include, among other things, current readings from one or more sensors of the sensor module, menus to navigate the various features of the personal monitoring device, time and date information, context-specific graphics and animations, and any other data available to or otherwise presentable by the personal monitoring device.

The I/O unit 212 may also include various output devices to facilitate various forms of output to a user in response to instructions from the processor 202. For example and without limitation, output devices of the personal monitoring device 102 may include a speaker through which audible tones may be played to alert or otherwise notify a user of various events or a vibration motor or similar haptic device to generate vibrations or other haptic outputs in response to various events. To facilitate the operation of such output devices, the I/O unit 212 may further include other electronic components, such as but not limited to digital-to-analog converters, to convert digital signals from the processor 202 to analog outputs of the output devices.

The personal monitoring device 102 further includes a power system 214 that generally provides power to the processor 202 and other components of the personal monitoring device 102.

Figure 3:
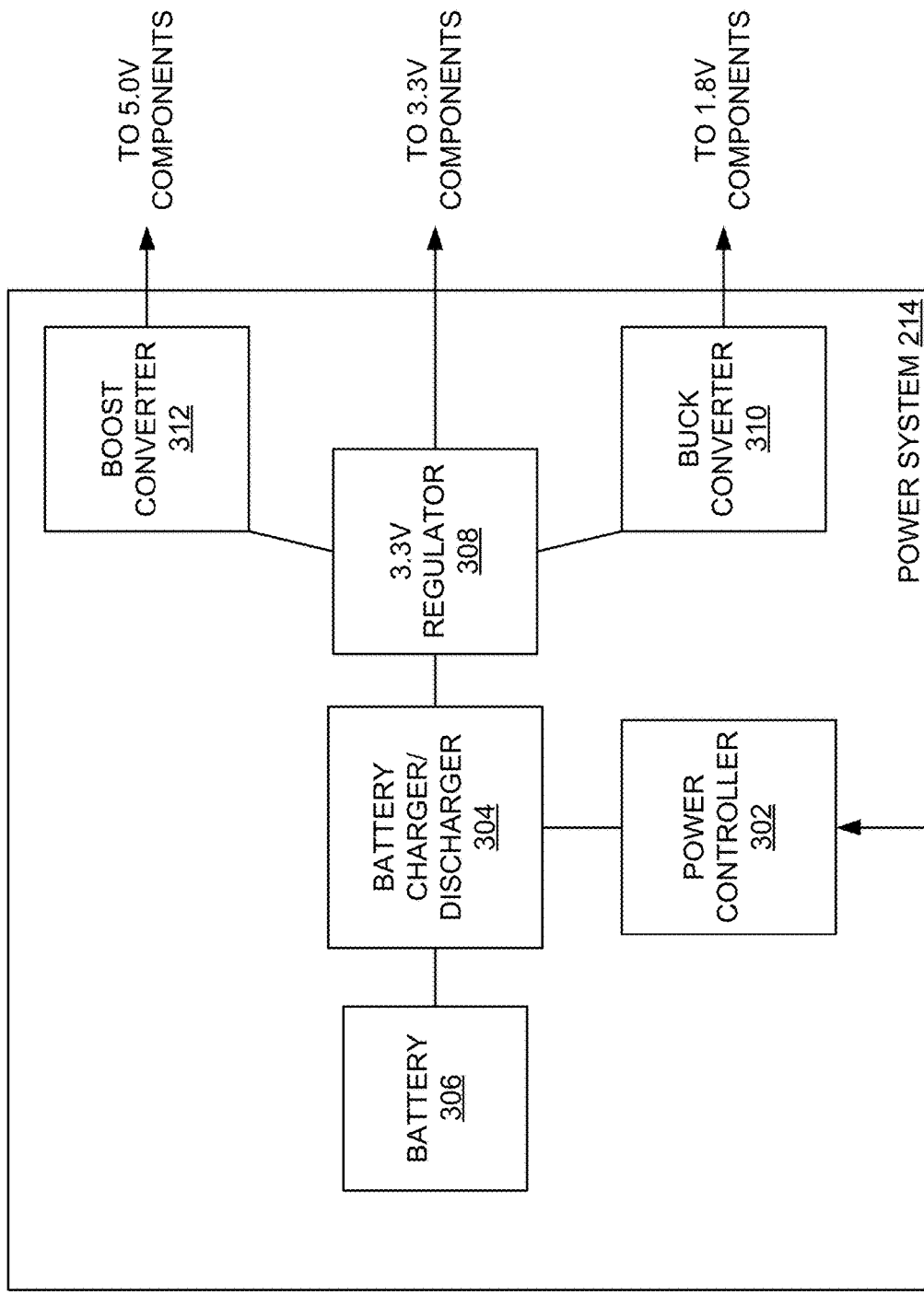
FIG. 3 is a block diagram illustrating an example power system of the personal monitoring device of FIG. 2.

FIG. 3 is a block diagram illustrating an example of the power system 214 in further detail. In general, the power system 214 may include a battery 306 or other power source and associated circuitry for managing charging and discharging of the battery to power components of the personal monitoring device 102. While various batteries types may be used, in at least certain implementations, the battery 306 is a rechargeable lithium ion (Li-ion) battery. Functionality of the power system 214 may generally be controlled by a power controller 302 in communication with the processor 202 of the personal monitoring device 102. However, in certain implementations, functionality of the power controller 302 may be performed by the processor 202 directly.

The power system 214 further includes a battery charger/discharger 304 adapted to monitor and control both charging of the battery 306 and distribution of power from the battery 306 to various components of the personal monitoring device 102. The battery charger/discharger 304 may facilitate charging of the personal monitoring device 102 in various ways. For example, in certain implementations, charging may be performed by plugging the personal monitoring device 102 into a wall outlet, computing device, or other power source. In other implementations, the personal monitoring device 102 may be charged by, among other things, inserting the personal monitoring device 102 into a docking station that in turn is plugged in to a power source, by inductive or other wireless charging methods, by a kinetic self-charging system that charges the battery 306 in response to movement of the personal monitoring device 102, or by solar cells (not shown) incorporated into the personal monitoring device 102. It should be appreciated that any of the foregoing charging methods may be used alone or in combination to provide power to the personal monitoring device 102.

As further illustrated in FIG. 3, the power system 214 may further include various components for modifying the power provided by the battery 306 via the battery charger/discharger 304. Although other arrangements are possible, the example of FIG. 3 includes circuitry for providing power at three separate voltages (1.8V, 3.3V and 5.0V) to accommodate various components of the personal monitoring device 102. More specifically, the power system 214 includes a regulator 308 for providing 3.3V and each of a buck converter 310 and a boost converter 312 for providing 1.8V and 5.0V, respectively.

Implementations of the present disclosure may include various features and functionality to balance battery life and functionality of the personal monitoring device 102. In general, such power management features include power management modes executable by the processor 202 of the personal monitoring device 102 to selectively activate and deactivate various components of the personal monitoring device 102 and/or to modify operation of the personal monitoring device 102 and its components to conserver power.

The personal monitoring device 102 may be configured to operate and transition between one or more power modes, each of which may correspond to a different level of functionality and power consumption (e.g., a "high" or "normal power mode" and one or more "low" or modified power modes). In certain implementations of the present disclosure, such power management techniques may be used to extend the charge of the battery 306 of the personal monitoring device 102 such that the personal monitoring device 102 may operate in a low or reduced power mode for a month or longer on a single charge.

Various components of the personal monitoring device 102 may generate heat and/or be impacted by the heat generated by other devices. Accordingly, the components of the personal monitoring device 102 may be arranged specifically to effectively manage heat flow. In one example, the personal monitoring device 102 may include one or more heat sinks or similar heat transfer elements to passively direct heat away from the internal components of the personal monitoring device 102. Such heat transfer elements may extend, at least in part, to an exterior surface of the personal monitoring device 102 to facilitate heat removal to the surrounding environment.

As another example, a temperature sensor (or other sensors that may be affected by heat generated by other components of the personal monitoring device 102) may be specifically located relative to other heat generating components. For example, the temperature sensor may be located on an outer edge of the personal monitoring device 102 opposite other heat generating components of the personal monitoring device 102. In other implementations, heat-sensitive sensors may be embedded in thermal insulation to thermally isolate such sensors from heat sources of the personal monitoring device 102.

Power management techniques according to the present disclosure may include, without limitation, modifying operation of sensors and other components of the personal monitoring device 102 based on their respective power consumption. For a sensor of the personal monitoring device 102, modifying the operation of the sensor may include, among other things, modifying a sampling rate of the sensor, activating or deactivating the sensor, modifying how frequently data is retrieved from the sensor, and the like. For communication-related components of the personal monitoring device 102 (such as those discussed above in the context of the communication unit 210), modifying operation may include, among other things, changing the frequency with which data is transmitted using a particular communication method or selectively enabling/disabling particular communication components (e.g., a cell chip). The operation of still other components of the personal monitoring device 102 may also be modified to conserve power. For example, the operation of a display of the personal monitoring device 102 may be modified by, among other things, controlling the frequency with which the display is used, the brightness/intensity of the display, and the duration for which the display is illuminated in response to an input received from the user. In certain modes, activation of the display may require input (e.g., a button press, swipe of the display, voice activation, facial recognition, or similar activity) to activate the display. The foregoing are simply examples of ways in which operation of components of the personal monitoring device 102 may be modified to conserve power and should be viewed as non-limiting examples.

In one example power management approach, the personal monitoring device 102 may automatically vary the rate at which samples are collected based on the movement speed of the personal monitoring device 102. To do so, the processor 202 may receive information from one or more of an accelerometer (other movement sensor) or a GPS unit (or similar location sensor) and determine to determine the movement speed of the user. The processor 202 may then scale the sampling rate of one or more of the sensors based on the speed of the user. As a result, the sensors operate at a relatively low sampling rate when the user is stationary or relatively stationary. As the user's movement increases, the user may be transitioning between environments more rapidly. To ensure that changes between such environments are properly captured, the sampling rate may be increased. In a similar method of power management, the personal monitoring device may enter a sleep or standby mode if the personal monitoring device 102 has not been moved or if movement of the personal monitoring device 102 is below a movement threshold for a particular amount of time. For example, if the personal monitoring device 102 has not been moved for approximately 5 minutes (or any other suitable time period), the processor 202 may automatically enter into a sleep/standby mode in which sampling for one or more sensors of the personal monitoring device 102 is significantly reduced (e.g., every 5 minutes or longer).

It should also be appreciated that different sensors may be managed differently depending on their relative power consumption characteristics. So, for example, relatively low power consumption sensors (such as barometric pressure sensors, CO sensors, temperature sensors, humidity sensors, and accelerometers) may be configured to operate at all times in a particular mode. In contrast, relatively high power consumption components (e.g., PM2.5 sensors, GPS sensors, and VOC sensors) may be configured to selective operate based on the current power mode or other factors. For example, such high power consumption sensors may collect data every ten minutes while stationary but increase sampling to every 30 seconds or more frequently when the personal monitoring device 102 is in motion.

Regarding communication, different methods of communication supported by the personal monitoring device 102 may be selectively activated and deactivated to control power consumption. In one example implementation, one or more communication units may be activated only if contacted by/paired with another device. For example, the personal monitoring device 102 may be configured to communicate and transmit data to a smart phone or similar computing device via an app or other software. While the personal monitoring device 102 may "listen" for pairing requests from such computing devices, the personal monitoring device 102 may only fully activate the corresponding communication unit/functionality in response to receiving such a request. In other implementations, certain communication units/functionality may only be activated in response to direct activation/deactivation commands from the user.

C. Example Personal Monitoring Device Form Factors and Features

FIGS. 4-7C illustrate different, non-limiting examples of personal monitoring devices in accordance with the present disclosure. Although each example device may be discussed as having a certain form factor and/or feature set, such device characteristics are provided merely as examples and, as a result, implementations of personal monitoring devices in accordance with the present disclosure are not to be limited to the specific example devices illustrated in FIGS. 4-7C and discussed below.

Figure 4:
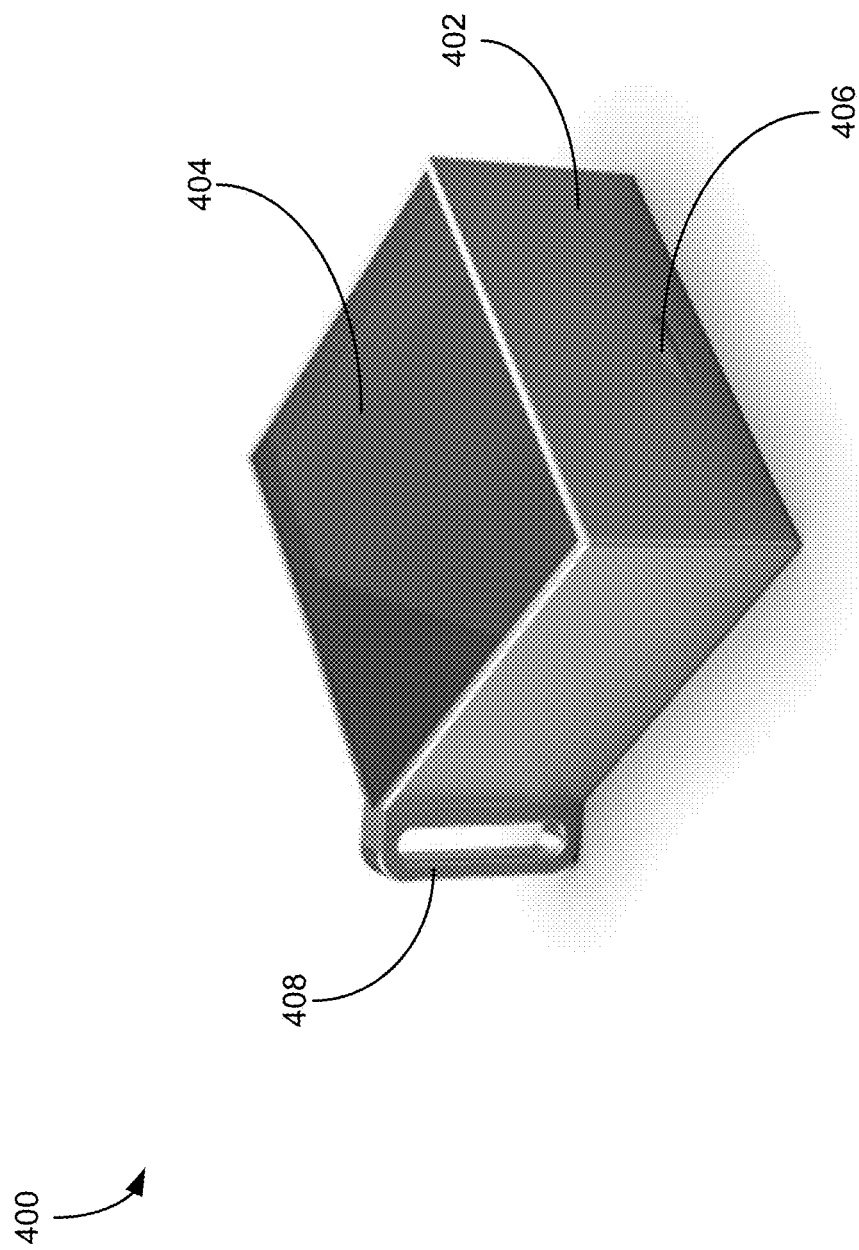
FIG. 4 is an isometric illustration of a first example personal monitoring device according to the present disclosure.

FIG. 4 is an isometric view of a first personal monitoring device 400 in accordance with the present disclosure. Although other form factors are possible, the personal monitoring device 400 is generally in the form of a wearable dongle or similar device that may easily worn by a user or attached to an accessory of the user. For example, as illustrated in FIG. 4, the personal monitoring device 400 has a substantially square profile having a diagonal dimension of about 3 inches or less and a thickness of approximately 1 inch or less. It should be appreciated that the shapes and dimensions discussed herein are provided merely as an example and other configurations are possible and fully contemplated within the scope of the present disclosure.

The personal monitoring device 400 includes a housing 402 containing the various components of the personal monitoring device 400. Among other things, the housing 402 couples to and supports a display 404. As illustrated in FIG. 4, the display 404 may occupy substantially one full side of the housing 402. As further illustrated, the housing 402 may define at least one opening 406 to permit air to enter the personal monitoring device 400. As noted above, such air may then be sampled and analyzed by various sensors disposed within the personal monitoring device 400. The analysis by the sensors may be used for various purposes including, without limitation, providing air quality metrics to a user of the personal monitoring device 400, logging and/or mapping of air quality within a particular location, monitoring environmental conditions that may be potentially harmful to the user, and the like. The housing 402 may further define various other openings and voids for other purposes. For example and without limitation, such openings may include ports for charging and/or transmitting data to or from the personal monitoring device 400, cavities for housing various sensors (e.g., photoelectric sensors or temperature sensors), and vents for facilitating air flow through the personal monitoring device 400 to aid in heat transfer and cooling of device components.

The personal monitoring device 400 may include a loop or similar attachment feature 408 for coupling the personal monitoring device 400 to another item or surface. For example, the attachment feature 408 may be adapted to receive a string, strap, clip, or similar feature of a piece of clothing or an accessory such that the personal monitoring device 400 may be worn or otherwise made easily portable. As illustrated in FIG. 4, the attachment feature 408 may be an integral loop formed into the housing 402 of the personal monitoring device 400. In other implementations, the attachment feature 408 may be selectively removable from the housing 402. In still other implementations, the attachment feature 408 may be a structural element on a face of the personal monitoring device 400, such as a groove or protrusion, configured to be received by a mating structural element of an item or surface.

The personal monitoring device 400 may generally be designed to withstand various environmental conditions and to meet various performance metrics. Without limitation, the personal monitoring device 400 may be designed to meet various metrics regarding water resistance/water proofing, corrosion resistance, ultraviolet light resistance, heat/cold resistance, drop/impact resistance, ingress protection, and the like. Various techniques may be used to meet such requirements including, without limitation, applying one or more coatings to portions of the personal monitoring device 400, insulating and/or sealing portions of the personal monitoring device 400, including filtration elements within the personal monitoring device 400, and the like.

Figure 5B:
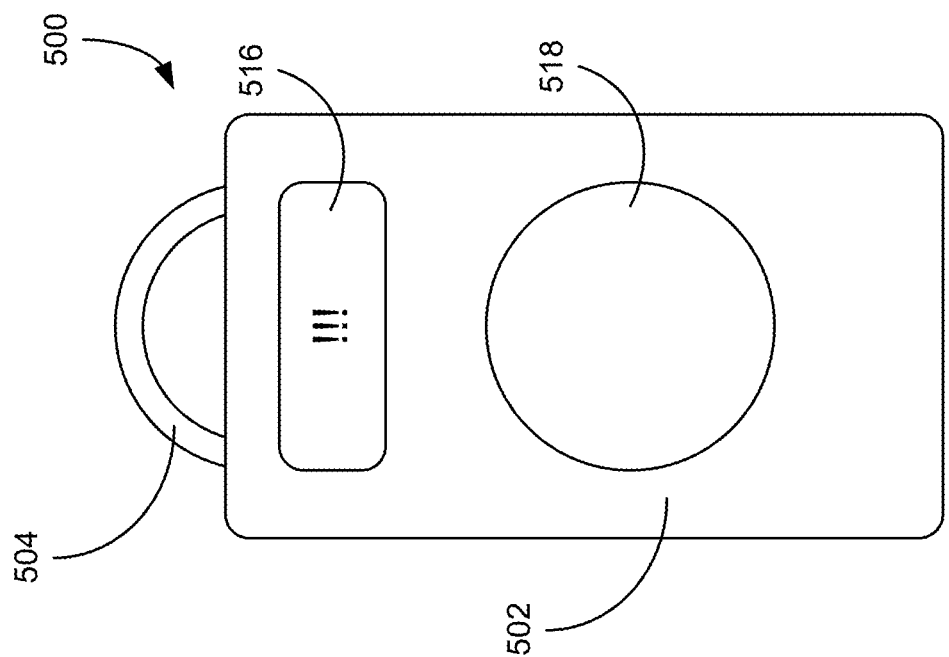
FIGS. 5A and 5B are front and rear views, respectively, a second example personal monitoring device according to the present disclosure.
Figure 5A:
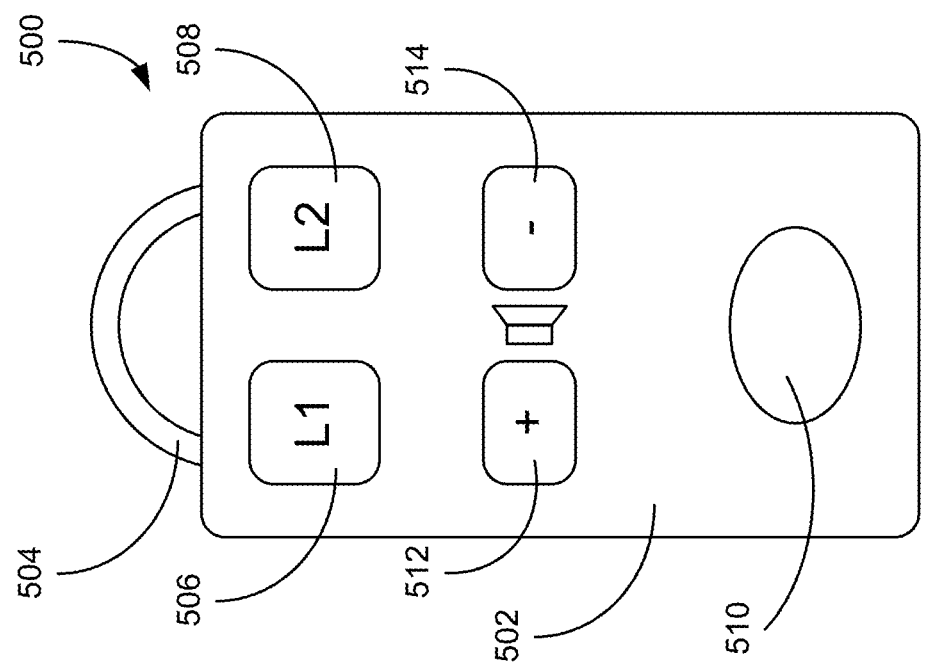

FIGS. 5A and 5B illustrate another example personal monitoring device 500 in the form of a key fob or similarly sized device. The personal monitoring device 500 is intended to illustrate a basic feature set that may be used in conjunction with systems according to the present disclosure. The personal monitoring device 500, similar to the personal monitoring device 400 of FIG. 4, may be configured to be readily attached to a key ring, backpack, or similar article for easy access.

Although the form and features of the personal monitoring device 500 may vary, the personal monitoring device 500 may be relatively small (e.g., approximately 2.5 inches by approximately 1 inch by approximately 0.75 inches) and may include a durable, waterproof housing 502. Although illustrated as having an integral loop as an attachment feature 504, the personal monitoring device 500 may include any suitable mechanism for attaching the personal monitoring device 500 to an article of clothing or accessory.

Similar to other personal monitoring devices discussed herein, the personal monitoring device 500 is designed to collect and transmit location, movement, and/or environmental data to a server (e.g., server system 104 of FIG. 1) and to facilitate two-way communication with one or more users of remote computing devices (e.g., remote computing device 106 of FIG. 1), such as a smart phone or similar computing device of a parent or guardian. To facilitate such functionality, the personal monitoring device 500 may include one or more sensor units for measuring location (e.g., a GPS module), movement (e.g., an accelerometer), and/or environmental conditions (e.g., an air quality sensor and/or a thermometer); one or more communication units (e.g., a 4G module); and suitable electronics for powering and controlling such units.

Regarding construction, the personal monitoring device 500 may be made from metal, plastic, or any other suitable material. The personal monitoring device 500 is preferably made of a material that is sufficiently durable to withstand both the regular forces and impacts associated with a user wearing the personal monitoring device 500, but also abnormal impacts that may arise in an accident/collision or similar situation. The personal monitoring device 500 is also preferably made from a material that is substantially resistant to wear, corrosion, or similar degradation (e.g., ultraviolet degradation), and is preferably waterproof to further protect internal components from damage.

To further protect the personal monitoring device 500 from ingress of moisture or other chemicals, the personal monitoring device 500 be entirely self-contained and lack any ports or similar access points. In such implementations, communication with the personal monitoring device 500 may be entirely wireless. Similarly, the personal monitoring device 500 may include a wireless (e.g., inductive) charging unit (including, e.g., a wireless charging plate 518, as shown in FIG. 5B) to enable charging of the personal monitoring device 500 without relying on a port or similar opening that may permit ingress of fluid or other matter.

Although the specific buttons/inputs included in the personal monitoring device 500 may vary, the specific implementation illustrated in FIGS. 5A and 5B includes two call buttons 506, 508, labelled "L1" and "L2", respectively. The call buttons 506, 508 may each be programmed or otherwise configured to automatically dial a specific phone number, such as the phone number of a parent or emergency contact, in response to being pressed. In other words, the personal monitoring device 500 may include preprogrammed phone numbers associated with each of the call buttons 506, 508 such that when pressed, the personal monitoring device 500 dials the preprogrammed number to initiate a call (e.g., using an internal communications module implementing 4G, cellular, Wi-Fi or other communications). As illustrated, the personal monitoring device 500 may also include a speaker and microphone 510 and associated volume buttons 512, 514 for facilitating communication when a call is established. In certain implementations, the speaker and microphone 510 may be covered with a hydrophobic mesh (not shown, or otherwise include a similar form of waterproofing), thereby maintaining ingress protection for the personal monitoring device 500.

As illustrated in FIG. 5B, the personal monitoring device 500 may also include an emergency call button 516. Similar to the call buttons 506, 508, the emergency call button 516 may cause the personal monitoring device 500 to automatically dial and establish a call with a preprogrammed phone number; however, the emergency call button 516 may be specifically configured to dial a phone number associated with emergency services (e.g., 9-1-1), a third-party dispatch and monitoring service, or similar services.

Figure 6B:
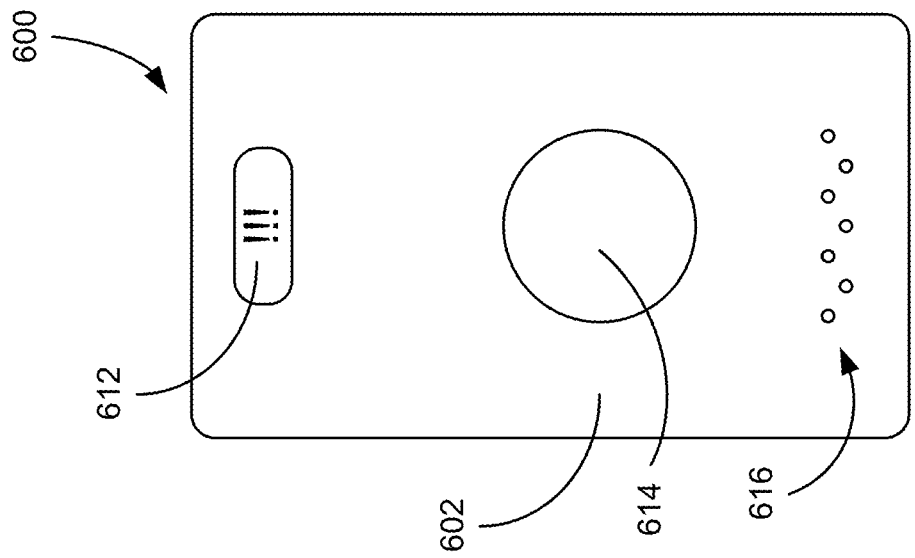
FIGS. 6A and 6B are front and rear views, respectively, of a third example personal monitoring device according to the present disclosure.
Figure 6A:
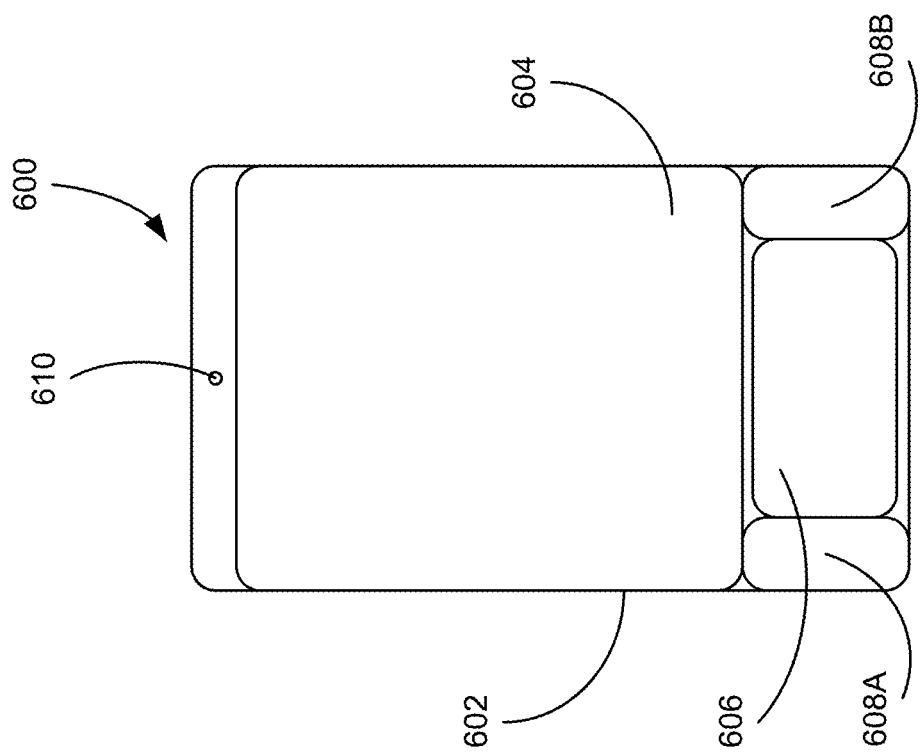

FIGS. 6A and 6B illustrate a third example personal monitoring device 600, which has a form factor of an electronic reader or similar device. As illustrated in FIG. 6A, the personal monitoring device 600 includes a housing 602, a display 604, an input pad 606, speakers 608A, 608B, and a microphone 610. As further illustrated in FIG. 6B, the personal monitoring device 600 further includes an emergency call button 612, a wireless charging pad 614, and vents 616.

Although the specific form and dimensions of the personal monitoring device 600 may vary, in at least certain implementations, the housing 602 may be relatively thin (e.g., less than about 0.25 inches) such that it can be readily stored in in a wallet, purse, binder, backpack, or similar item.

To improve overall battery life, in at least some implementations, the display 604 may be a low power display, such as an electronic ink display.

The input pad 606 may be a touchpad or similar input device for controlling and providing input to the personal monitoring device 600. In certain implementations, the input pad 606 may be replaced or supplemented by other input devices such as, but not limited to, one or more buttons, directional pads, scroll wheels, or similar input devices. The personal monitoring device 600 may also include additional buttons disposed elsewhere on the housing 602 to provide additional functionality. For example and without limitation, such functionality may include dialing predefined phone numbers (similar to the call buttons 506, 508 of the personal monitoring device 500 of FIGS. 5A and 5B), controlling volume of the personal monitoring device 600, or performing similar functions. As illustrated in FIG. 6B, the personal monitoring device 600 may also include a dedicated emergency call button 612, similar to the emergency call button 516 of the personal monitoring device 500 of FIGS. 5A and 5B.

Similar to the personal monitoring device 500 of FIGS. 5A and 5B, the personal monitoring device may include one or more speakers 608A, 608B and a microphone 610 for facilitating voice-based communication, such as with a remote computing device. The speakers 608A, 608B and microphone 610 may also be used as alternative or additional output and input devices for receiving information from and providing input to the personal monitoring device 600. For example and among other things, the speakers 608A, 608B may be used to provide audio signals or alerts to a user in response to a change in the user's location, a change in the user's environment, or other similar event. As another example, the microphone 610

As illustrated in FIG. 6B, the personal monitoring device 600 may include one or more vents 616 to facilitate airflow within the housing 602. Such airflow may be used, for example, to provide air to be sampled and analyzed by one or more air quality sensors (not shown) disposed within the housing 602. The vents 616 may also be arranged and configured to facilitate cooling and ventilation of heat-generating components within the housing 602.

FIGS. 7A-7C illustrate a fourth example personal monitoring device 700 having a form factor akin to a smartphone or similar mobile device. As illustrated in FIG. 7A, which is a front view of the personal monitoring device 700, the personal monitoring device 700 may include a housing 702 supporting a display 704, which may be a touchscreen display. The personal monitoring device 700 may further include additional physical buttons to enable input to the personal monitoring device 700. For example and without limitation, the personal monitoring device 700 includes a "home" button 706 that may be used for various purposes including returning to a main menu of a user interface executed by the personal monitoring device 700. As shown in FIG. 7C, which is a rear view of the personal monitoring device 700, the personal monitoring device 700 may also include an emergency call button 708 and a wireless charging plate 710, similar to those of the previously discussed example devices. Although not illustrated in FIGS. 7A-7C, the personal monitoring device 700 may further include one or more speakers and a microphone for facilitate audio input and output. Referring to FIG. 7B, which is a side view of the personal monitoring device 700, the personal monitoring device 700 may include vents or similar openings 712 to facilitate air exchange between the surrounding environment and an internal volume of the personal monitoring device 700. As previously discussed the openings 712 may be used to facilitate sampling by air quality sensors and/or to facilitate cooling of internal components of the personal monitoring device 700.

In addition to the foregoing features and functions described in the context of FIGS. 4-7C, personal monitoring devices in accordance with the present disclosure may also include or support other features and functions. Such features and functions may include, without limitation, GPS navigation, generation and transmission of preset text-based messages (e.g., SMS messages, emails, etc.), alarm clock functionality, storage and editing of contact lists, and blocking of messages and calls received from device or numbers not included in a contact list, or any other features and functions described herein.

D. Variable Sampling Rate and Power Conservation Functions

In certain implementations of the present disclosure, the personal monitoring device 102 may have a variable rate at which sensor data is sampled and provided to the server system 104. Among other things, a variable rate may be useful in conserving power and extending battery life of the personal monitoring device 102. For example, while the personal monitoring device 102 is within a defined environment, the personal monitoring device 102 may be configured to sample and transmit sensor data at a first sample rate. However, if the personal monitoring device 102 exits the defined environment, the sampling rate may be automatically changed to a second sampling rate such that the personal monitoring device 102 reports sensor data more frequently.

In general, control of the sampling rate of the personal monitoring device 102 is based, at least in part, on communications received from the server system 104 in response to sensor data provided by the personal monitoring device 102. In one specific example, the personal monitoring device 102 may transmit location data to the server system 104 at a first sampling rate. The server system 104 then analyzes the location data to determine if one or more location-based conditions are met. Such conditions may include, among other things and without limitation, the location data indicating that the personal monitoring device 102 is within/outside of a defined area, within/outside of a defined proximity to a geographic area or feature, within/outside of a defined proximity relative to another computing device or person, and the like. In response to determining the location-based condition is met, the server system 104 may then transmit a reconfiguration message to the personal monitoring device 102 that causes the personal monitoring device 102 to begin sampling at a second sampling rate different than the first sampling rate. So, for example, while a child user of the personal monitoring device 102 is on school property, the personal monitoring device 102 may have a first, relatively low sampling rate (e.g., once every ten minutes). However, if the personal monitoring device 102 is subsequently moved off of school property, the personal monitoring device 102 may have a second, higher sampling rate to permit closer monitoring of the child's movement.

Figure 8:
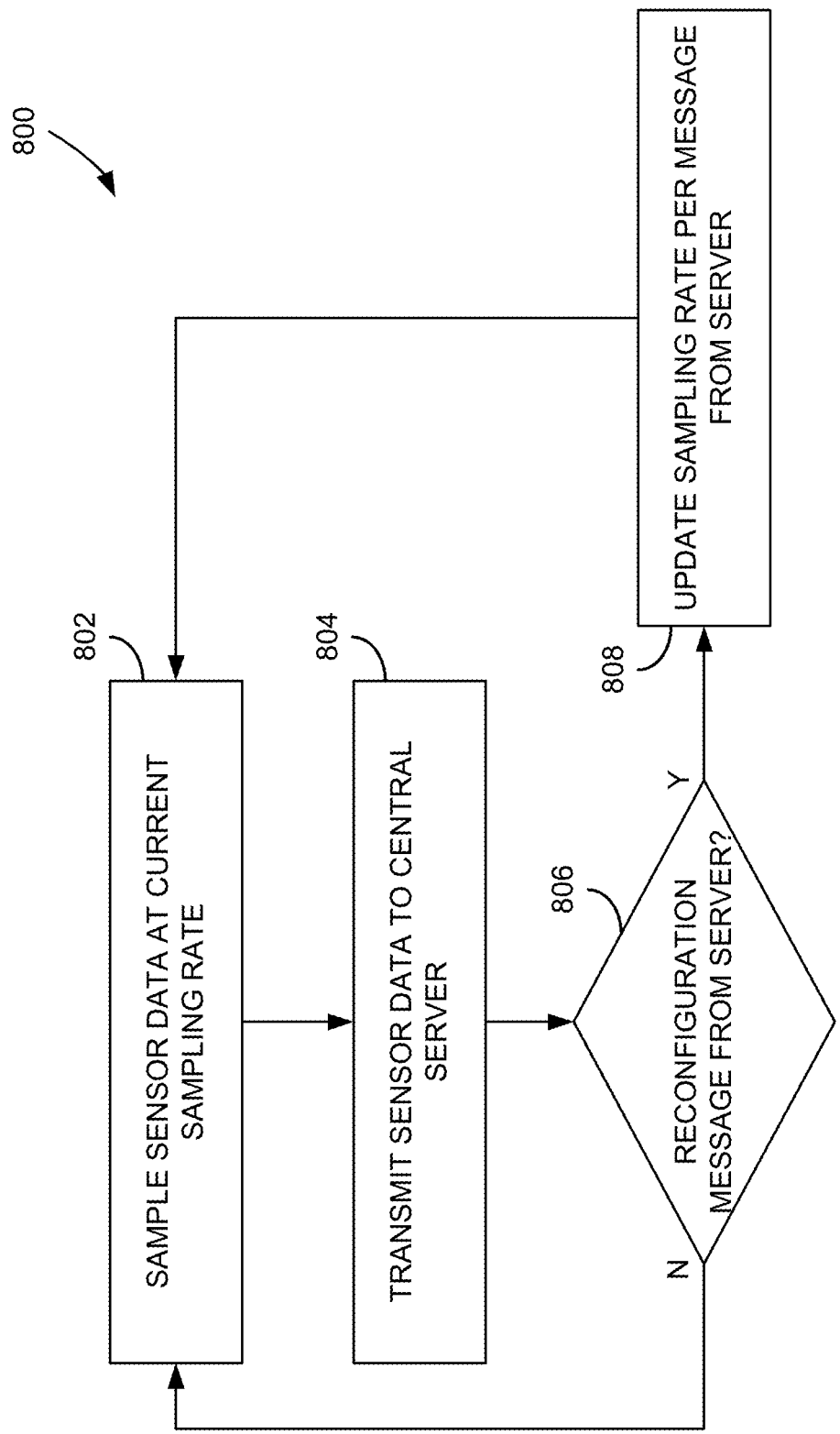
FIG. 8 is a flow chart illustrating an example method of transmitting sensor data from a personal monitoring device according to the present disclosure.
Figure 9:
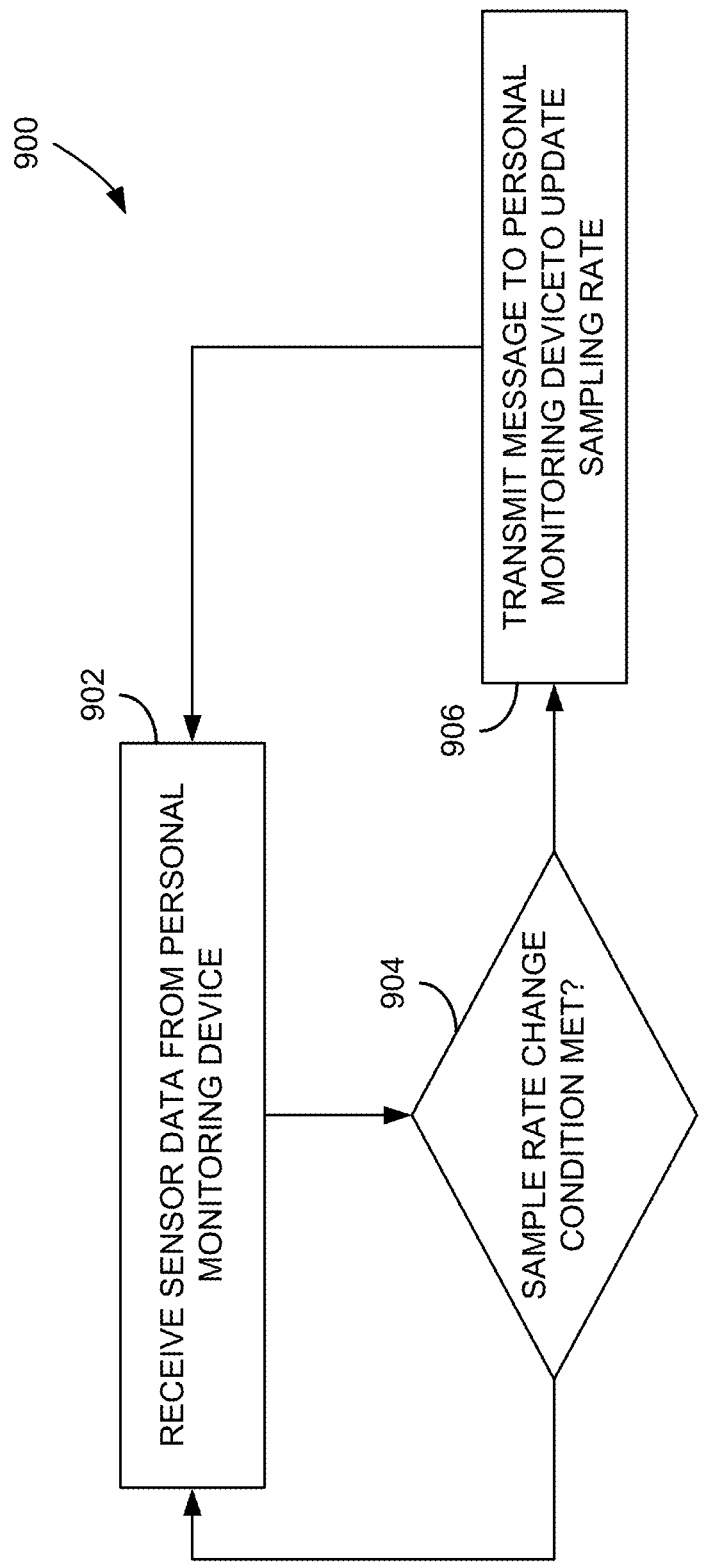
FIG. 9 is a flow chart illustrating an example method of receiving and processing data sensor data at a server from a personal monitoring device in accordance with the present disclosure.

The foregoing process is illustrated in FIGS. 8 and 9, which provide methods 800, 900 for implementing variable sampling rates from the perspective of the personal monitoring device 102 and the server system 104, respectively.

Referring first to FIG. 8, the personal monitoring device 102 begins operation at a first sampling rate. To do so, the personal monitoring device 102 samples sensor data from one or more sensor of the personal monitoring device 102 (operation 802) and transmits the sampled sensor data to the server system 104 (operation 804). The personal monitoring device 102 may then periodically check if a reconfiguration message has been received from the server system 104 (operation 806). If a reconfiguration message has not been received, the personal monitoring device 102 continues to provide sensor data at the current sampling rate (operations 802, 804). If, on the other hand, a reconfiguration message has been received, the personal monitoring device 102 updates its sampling rate according to the reconfiguration message (operation 808) before continuing to sample and provide sensor data to the server system 104 at the updated sampling rate. Notably, while illustrated in FIG. 8 as occurring after transmission of sensor data to the server system 104, the operation of checking for reconfiguration messages (operation 806) and updating the sampling settings of the personal monitoring device 102 (operation 808) may also occur in parallel with or as a separate routine from general sampling and transmission by the personal monitoring device 102.

Referring now to the method 900 of FIG. 9, the server system 104 receives sensor data from the personal monitoring device 102 (operation 902). The server system 104 then determines whether the received sensor data meets a condition for reconfiguring the personal monitoring device 102 by changing a sample rate of the personal monitoring device 102 (operation 904). If not, the server system 104 continues to receive and process sensor data form the personal monitoring device 102 at the current sampling rate. If the sample rate change condition is met, however, the server system 104 transmits a reconfiguration message to the personal monitoring device 102 including an indication of a new sampling rate (operation 906). When received by the personal monitoring device 102, the reconfiguration message causes the personal monitoring device 102 to updates its current configuration to begin sampling sensor data at the rate specified in the reconfiguration message.

In certain implementations, the sensor data provided by the personal monitoring device 102 (e.g., in operations 802 and 804 of FIG. 8) and received and analyzed by the server system 104 (e.g., in operations 902 and 904) can be any sensor data that may be collected by sensors of the personal monitoring device 102 and may include sensor data from one or more sensors of the personal monitoring device 102. The sensors from which the sensor data is obtained may include, without limitation, location-based sensors or location-based sensor systems (e.g., a GPS systems), motion-based sensors (e.g., an accelerometer), environmental sensors (e.g., a thermometer or an air quality sensors), or any other sensor that may be included in the personal monitoring device 102. In implementations in which sensor data is collected from multiple sensors, the personal monitoring device 102 may sample each sensor or groups of sensors at different sampling rates. In such implementations, each sampling rate may be independently modified or configurable by messages received from the server system 104.

In certain implementations, the sensor data provided to the server system 104 may correspond to the sensor for which the server system 104 reconfigures the sampling rate. For example, the server system 104 may receive location data from the personal monitoring device 102 at a first sampling rate and the server system 104 may transmit a reconfiguration message to the personal monitoring device 102 to provide location data at a second sampling rate. However, in other implementations, the type of sensor data received and processed by the server system 104 may be different than the type of sensor data for which the sampling rate is modified by the server system 104. For example, the sensor data collected and processed by the server system 104 may include environmental (e.g., air quality) or movement (e.g., acceleration) data. Although the server system 104 may decide to update sampling rates based on the environmental or movement data, the updated sampling rate may be that of a location sensor. In one example of such an implementation, the server system 104 may determine when a user of the personal monitoring device 102 enters an area with poor air quality based on sensor data provided by an air quality sensor of the personal monitoring device 102, but may then transmit a message to the personal monitoring device 102 that increases a sampling rate of a location sensor of the personal monitoring device 102.

It should also be noted that while the personal monitoring device 102 may be configured to provide sensor data on a periodic basis to the server system 104, the personal monitoring device 102 may further be configured to receive and process requests for sensor data from the server system 104. As discussed below in the context of FIG. 12, in at least certain implementations, such requests may be in response to requests from a remote computing device (such as the remote computing device 106) received by the server system 104.

As noted above in operation 806 of method 800 and operation 906 of method 900, implementations of the present disclosure include the exchange of reconfiguration messages between the server system 104 and the personal monitoring device 102. In general and among other things, reconfiguration messages sent by the server system 104 cause the personal monitoring device 102 to modify a sampling rate of the monitoring device 102. Reconfiguration messages may be transmitted using any suitable communication protocol and may have any suitable message format. In certain implementations, the reconfiguration messages may include a sampling rate indicator corresponding to the new sampling rate. The sampling rate indicator may be a numerical value directly corresponding to the new sampling rate, e.g., a number expressed in a number of samples per minute or time between samples. As another example, the value contained in the reconfiguration may be correlated to a sampling rate. So, for example and without limitation, a "1" may indicate a sampling rate of 10 seconds between samples, a "2" may indicate a sampling rate of a minute between samples, and a "3" may indicate a sampling rate of five minutes between samples.

In implementations in which the personal monitoring device 102 includes multiple sensors, the reconfiguration message may also include an indicator identifying the particular sensor or groups of sensors to be reconfigured in response to the reconfiguration message. For example, each sensor of the personal monitoring device 102 may be assigned an index (e.g., "1" for the location sensor, "2" for the accelerometer, etc.). The reconfiguration message may then include a first character indicating the sensor to be reconfigured and a second character indicating how the sensor is to be reconfigured. So, for example and using the foregoing example indices, a message with content "23" would reconfigure the accelerometer of the personal monitoring device 102 to provide data at a rate of once per every five minutes.

The foregoing examples of reconfigurations messages are merely intended to provide one example of reconfiguration messages according to implementations of the present disclosure. Nevertheless, the foregoing example is an efficient approach to facilitating communication between the personal monitoring device 102 and the server system 104. More generally, however, communication between the personal monitoring device 102 and the server system 104 use any suitable message format, protocol, communication medium, etc.

As noted above, in at least certain implementations, power management of the personal monitoring device 102 may include modifying the frequency with which data is transmitted from the personal monitoring device 102 to the server system 104 and/or whether the personal monitoring device 102 periodically transmits data to the server system 104 or only transmits data in response to a request from the server system 104.

Figure 10:
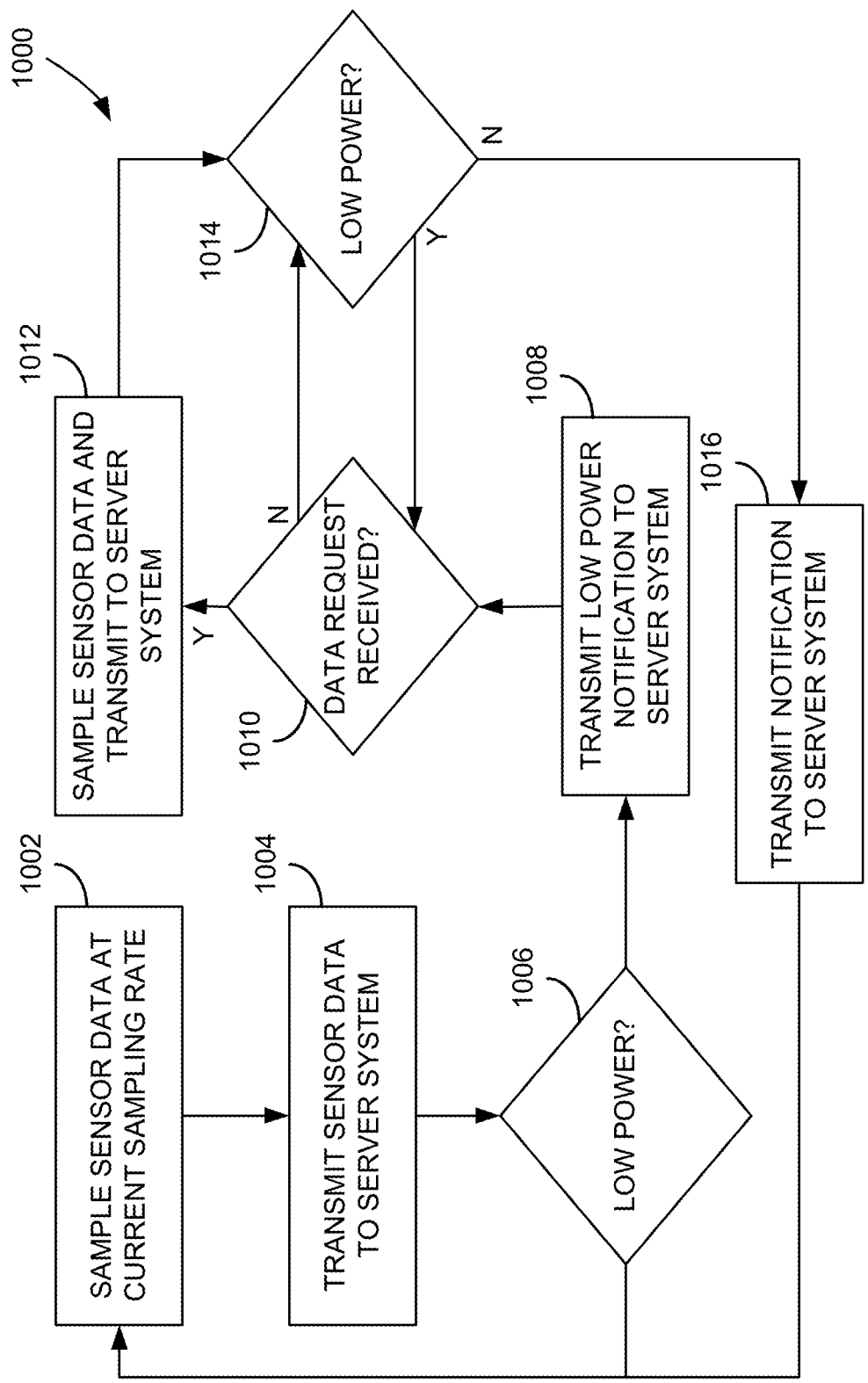
FIG. 10 is a flow chart illustrating an example method of low power operation of a personal monitoring in accordance with the present disclosure.
Figure 11:
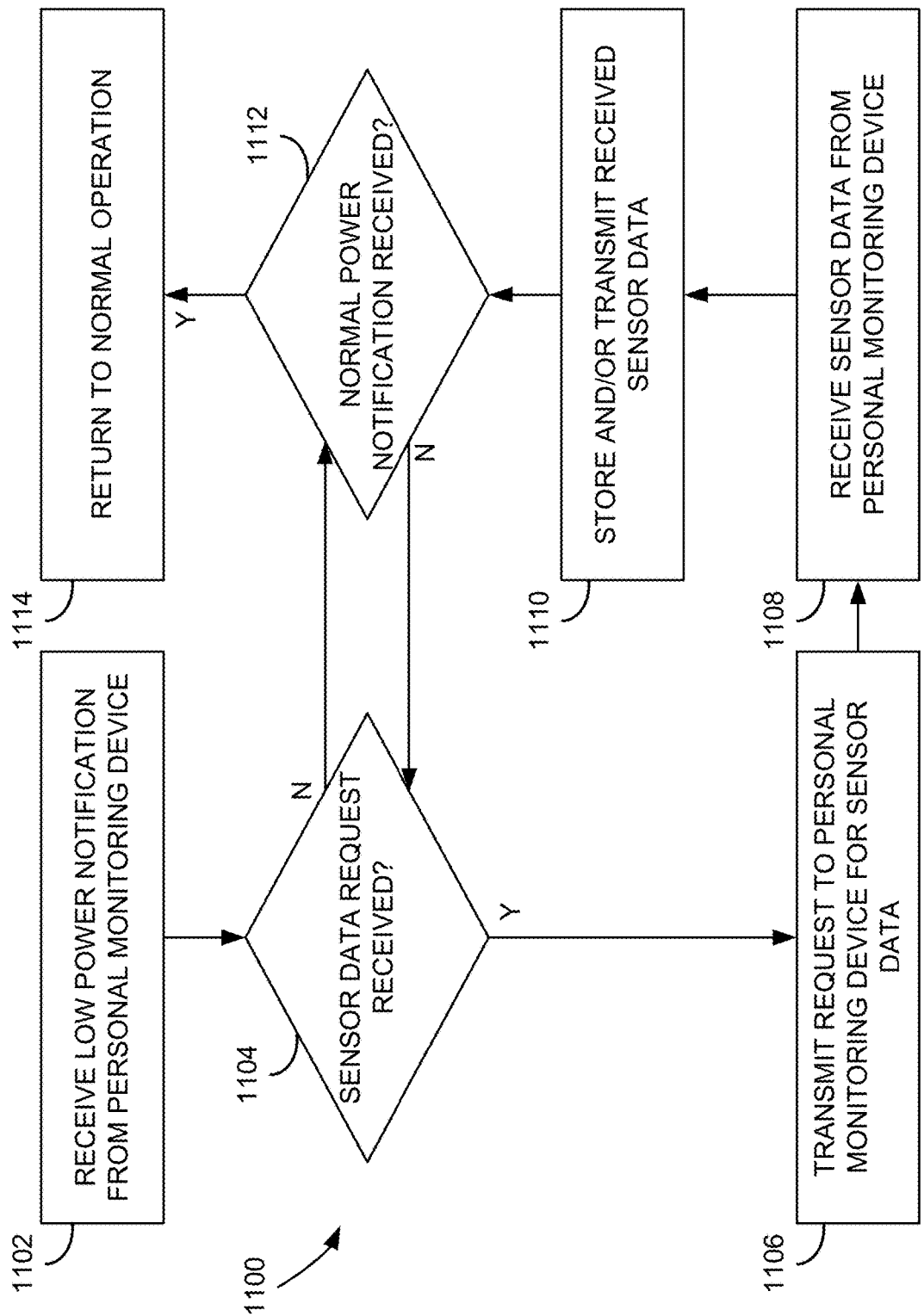
FIG. 11 is a flow chart illustrating an example method of operating a server in conjunction with a personal monitoring device.

An example of the latter approach is provided in FIGS. 10 and 11. More specifically, FIG. 10 is a flow chart illustrating a method 1000 for operating the personal monitoring device 102 in a low power mode from the perspective of the personal monitoring device 102. Similarly, FIG. 11 is a flow chart illustrating a method 1100 for operating the personal monitoring device 102 in a low power mode from the perspective of the server system 104.

Referring first to FIG. 10, the personal monitoring device 102 begins in a normal operating mode. More specifically, the personal monitoring device 102 samples sensor data at a current sampling rate (operation 1002) and then transmits the collected sensor data to the server system 104 for processing, storage, analysis, etc. (operation 1004).

As the personal monitoring device 102 collects and transmits the sensor data, it may generally monitor the remaining charge left in a battery 306 (shown in FIG. 3) or similar energy storage device of the personal monitoring device 102 to determine when the power level drops below a particular threshold (operation 1006). Although the specific threshold may vary, in at least certain implementations, the personal monitoring device 102 may be considered to have low power when the battery charge is below 50%, below 40%, below 30%, below 25%, below 10%, or below any other suitable threshold.

While the power level of the power source for the personal monitoring device 102 remains above the low power level, the personal monitoring device 102 may continue to collect and transmit sensor data at the current sampling rate (e.g., by repeating operations 1002 and 1004). When a low power condition is met, however, the personal monitoring device 102 may transition into a low power mode in which the personal monitoring device 102 stops continuous transmission of sensor data to the server system 104 and instead only provides sensor data upon request.

To do so, the personal monitoring device 102 may transmit a "low power" notification to the server system 104 (operation 1008). The low power notification generally indicates to the server system 104 that the personal monitoring device 102 will no longer be transmitting sensor data to the server system 104 and that the server system 104 must now submit requests to the personal monitoring device 102 to receive sensor data from the personal monitoring device 102.

As illustrated in FIG. 10, the personal monitoring device 102 may poll for or otherwise wait for data requests from the server system 104 (operation 1010) and periodically check whether the low power condition has been alleviated (operation 1014), such as by charging of the personal monitoring device 102. If a data request is received, the personal monitoring device 102 samples the corresponding sensor data and transmits the sensor data to the server system 104 (operation 1012). After responding to a request from the server system 104, the personal monitoring device 102 may revert to checking the device power condition (operation 1014) and waiting/checking for requests from the server system (operation 1010). When the low power condition is alleviated, the personal monitoring device 102 may transmit a corresponding notification to the server system (operation 1016) before returning to normal operation in which the personal monitoring device 102 periodically samples and transmits sensor data to the server system 104 at the current sampling rate.

FIG. 11 illustrates a similar method 1100 for low-power operation of a personal monitoring device, such as the personal monitoring device 102, from the perspective of a server system, such as the server system 104 of FIG. 1.

The method 1100 first includes the server system 104 receiving a notification from the personal monitoring device 102 that the personal monitoring device 102 has entered into a low power mode (operation 1102).

Subsequently, the server system 104 may determine whether the server system 104 has received a request for sensor data from the personal monitoring device 102 has been received (operation 1104). Such a request for sensor device may be received, for example, from a remote computing device, such as the remote computing device 106 of FIG. 1, or may be internally generated/initiated by the server system 104. While waiting for a request, the server system may also determine whether the server system 104 has received a notification from the personal monitoring device 102 indicating that normal operation of the personal monitoring device 102 has been restored (e.g., due to the personal monitoring device 102 being charged).

In response to receiving a request for sensor data, the server system 104 may generated and transmit a request for the sensor data to the personal monitoring device 102 (operation 1106). The server system 104 may then receive the requested sensor data from the personal monitoring device (operation 1108) and may then store and/or transmit the received sensor data. For example, the server system 104 may store the received sensor data in a data source of the server system 104 or otherwise accessible to the server system 104. In addition to or instead of storing the received sensor data, the server system 104 may also transmit the received sensor data to a remote computing device, such as the remote computing device 106, which may or may not be the same device from which a request is received in operation 1102.

The foregoing process may be repeated until a notification is received indicating that personal monitoring device 102 has exited the low power state and returned to normal operation (operation 1112). More specifically, in response to receiving such a notification, the server system 104 may similarly return to normal operation (operation 1114), which, in certain implementations may include the server system 104 receiving and processing sensor data periodically provided by the personal monitoring device, such as described above in the method 900 of FIG. 9.

E. On-Demand Sensor Data Retrieval

Figure 12:
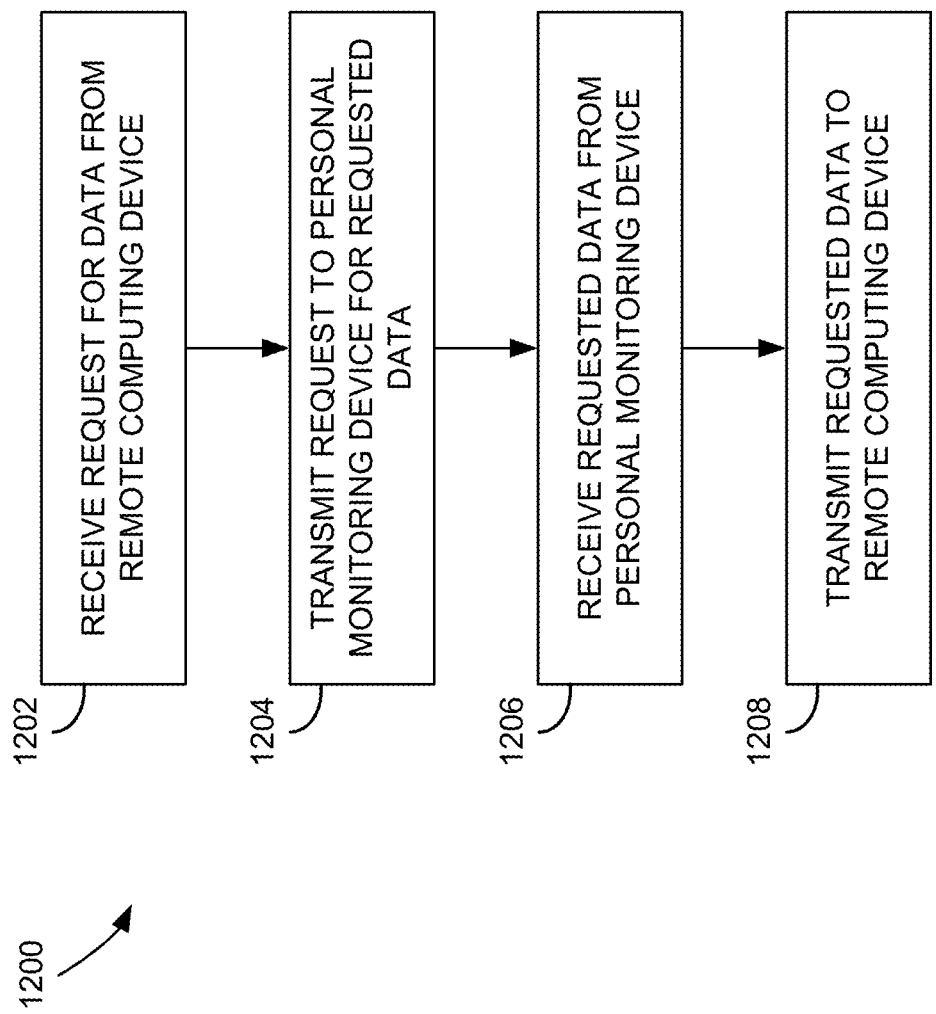
FIG. 12 is a flow chart illustrating an example method of processing a request for sensor data from a remote computing device.

As noted above, the server system 104 may be configured to receive and process data requests from other computing devices, such as the remote computing device 106. FIG. 12 illustrates an example method 1200 directed to the processing of such requests. The method 1200 begins by the server system 104 receiving a request for data from the remote computing device 106 (operation 1202). In response, the server system 104 generates and transmits a request for the corresponding sensor data to the personal monitoring device (operation 1204) and subsequently receives the requested data from the personal monitoring device (operation 1206). The server system 104 may then transmit the requested data to the remote computing device for presentation to a user of the remote computing device (operation 1208).

In one specific implementation, a parent or similar user of the remote computing device 106 may transmit a request to the server system 104 for the current location and environmental readings from a personal monitoring device 102 associated with a child. Such a request may be submitted, for example, through an app, portal, website, or other software executed on the remote computing device 106. In response to the request, the server system 104 generates and transmits a second request message to the personal monitoring device 102, which then provides the requested location and environmental data to the server system 104. The server system 104 then transmits the sensor data to the remote computing device 106 for presentation to the user of the remote computing device 106.

The method of FIG. 12 illustrates on-demand retrieval of live sensor data from the personal monitoring device, however, in at least certain implementations, the server system 104 may also be configured to provide historical sensor data to the remote computing device 106. In certain implementations, such sensor data may include the actual data values collected by the server system 104 from the personal monitoring device 102; however, in other implementations, the sensor data provided for presentation via the remote computing device 106 may include a summary of historical data.

Data may be presented via the remote computing device 106 in any suitable manner. However, in at least one example implementation, sensor data provided by the personal monitoring device 102 may be displayed or otherwise overlaid on a map or similar graphic indicating the location of the personal monitoring device 102. Such a map or graphic may be displayed, for example, by a user interface of an app, website, or program executed by the remote computing device 106. To the extent the remote computing device 106 is paired or associated with multiple personal monitoring devices, similar indicators or graphics may also be included for each personal monitoring device. In other implementations, the sensor data may be presented in tabular, graphical, or similar format that may include historical trends of the sensor data.

F. Additional Features and Functionality i. Environmental Mapping

In addition to the foregoing functionality, personal monitoring devices according to the present disclosure may be used to provide what is referred to herein as environmental mapping. In general, environmental mapping refers to the process of correlating location and sensor data to provide high-resolution maps including or overlain with air quality or other similar environmental information. For purposes of the following discussion, air quality is used as an example of environmental conditions that may be mapped, however, it should be appreciated that air quality is provided merely as an example and other environmental conditions may be mapped in a similar fashion.

To provide environmental mapping, a server or similar central computing system (e.g., server system 104 of FIG. 1) collects data from multiple personal monitoring devices (e.g., personal monitoring device 102 of FIG. 1) and, in particular, sensor readings from environmental sensors of such devices that further include location data. In addition to the data collected from the personal monitoring devices, additional data from mapping, weather, or other similar services (e.g., from external computing system 116 of FIG. 1) may also be integrated into the system to supplement the data collected from the personal monitoring devices.

Based on the data collected by the server system, a data set may be generated that correlates various air quality metrics with geographic locations. Such a data set may then be used to generate maps or other graphical representations of the air quality metrics. For example, the data set may be used to generate one or more map overlays that provide a heat-map or similar visualization of the collected air quality data.

In one example application, the data set may be used to provide a graphical user interface in which a dynamically navigable map can be overlain with one or more of PM2.5, pollen, VOC, CO, temperature, humidity, or other such information. A user of the interface may selectively toggle one or more of the overlays to visually display the corresponding metric. The user may also be able to select a specific location or area and receive detailed information regarding environmental conditions in the identified location.

In certain cases, the data set may be accessible, such as through a web service or one or more application programmer interfaces (APIs), for integration into other mapping and environmental applications. One example of such an application is a real estate application or website. Such a website may access and retrieve the environmental mapping data set to provide environmental information for homes and neighborhoods to supplement pricing, school, taxation, valuation, and similar information that is conventionally.

ii. Advanced User Alerts and User Profiles

As previously discussed, implementations of the present disclosure may include systems configured to generate and transmit alerts in response to certain events measured by sensors of personal monitoring devices. For example, in response to measuring an environmental condition (e.g., pollutant levels), movement (e.g., acceleration associated with a fall), or location that indicates an emergency or potential emergency situation, a server system in communication with the personal monitoring device and/or the personal monitoring device itself may transmit alerts or initiate calls with other remote systems and devices. More generally, such alerting mechanisms include detecting an event or environmental condition and, in response to identifying the event of condition, performing a corresponding action.

In some implementations of the present disclosure, a multi-level alert and notification mechanism may be implemented. Such a system may include, for example, varying responses based on a severity of an event or condition detected by the personal device or server system. In certain implementations, the personal monitoring device or server system may also be configured to provide a range of responses that escalate unless the user of the personal monitoring device demonstrates responsiveness by providing an acknowledgement (e.g., by swiping or touching the screen of the device, by issuing a voice command, by pressing a button, or by any other suitable input to the device) within a corresponding time period.

The thresholds used to identify potentially harmful conditions or events and the corresponding responses may be modified based on characteristics of the user of the personal monitoring device. Such characteristics may be provided to or otherwise made available to the personal monitoring device, such as by a cloud-based storage system. For example, the personal monitoring device of a user with a respiratory disease may be configured to have lower thresholds associated with air quality and/or more elevated responses when air quality/pollutant thresholds are exceeded as compared to a personal monitoring device for a user without a respiratory condition or with a less severe respiratory condition. As another example, the device of an elderly user may be configured to have a similar lower threshold or elevated response for fall-related events, e.g., as measured based on acceleration of the personal monitoring device.

It should be appreciated that the environmental conditions and events may correspond to any parameter measurable by the personal monitoring device. Moreover, the thresholds for detecting conditions and events may be based on any of absolute measurements, relative measurements, average measurements (e.g., average measurements over time), absolute changes in measurements, relative changes in measurement, or any other measurable change in a parameter measureable by the personal monitoring device.

Although other implementations are possible, the following description provides an illustrative example of a multi-level response implementation in which actions in response to a particular condition or event are gradually increased until and unless such actions are acknowledged by a user of the personal monitoring device. A similar arrangement of escalating actions may be used, for example, in conjunction with different thresholds for a particular parameter measureable by the personal monitoring device. The following example actions may be implemented in combination or individually in any personal monitoring device or system according to the present disclosure and for any parameter measurable by the personal monitoring device. Moreover, the actions discussed below are merely exemplary and other actions are possible.

With the foregoing in mind, the example implementation of an action and response system is generally described below as being divided into action levels, with the personal monitoring device and associated system initiating elevating actions as the action level increases. As previously noted, in one implementation the transition between action levels generally occurs after a certain time has elapsed at a particular action level without the personal monitoring device receiving an acknowledgement from the user. The time between each action level may vary and may, in certain instances, be based on or otherwise customized based on the user of the personal monitoring device.

At a first action level of the example case, an initial warning may be provided to a user via one of the output mechanisms of the personal monitoring device. For example, such a warning may be provided in the form of an audible tone or a vibration produced by suitable output mechanisms of the personal monitoring device. Assuming the user has not acknowledged the initial warning, the personal monitoring device may transition to a subsequent, higher action level in which the output from the personal monitoring device is intensified (e.g., the volume and/or duration of the audible tone or the intensity of the vibration is increased, an audio message may be played to try and get the user's attention, etc.). If the user still fails to respond, the action level may again be elevated, such as by playing audio messages at a volume or intensity directed to alerting passersby.

If acknowledgement is still not received by the personal monitoring device, the personal monitoring device may initiate a remote communication. For example, the personal monitoring device may generate and send an email, a text message, or similar notification to various recipients. Such recipients may include one or more predefined contacts (e.g., parents, guardians, caretakers, or other individuals) or a monitoring service associated with the personal monitoring device. In certain implementations, the personal monitoring device may subsequently contact emergency services, such as by calling 911, in the event the action level is again elevated.

In addition to the previously discussed functions and applications, personal monitoring devices and systems described herein may be configured to provide various other functions. As evidenced by the following examples, such functions may include but are not limited to additional health and safety-related applications. More generally, the personal monitoring devices and associated systems herein may be used in applications requiring a compact, energy efficient, and highly flexible sensor and communication platform. Accordingly, the following examples should be regarded as non-limiting applications of the personal monitoring device and associated system.

With reference to the network environment 100 of FIG. 1, in certain implementations of the present disclosure, the server system 104 may be configured to generate and transmit alerts on behalf of the personal monitoring device 102 and, in particular, in response to a user of a personal monitoring device 102 in response to sensor data received from the personal monitoring device 102. In certain implementations, the sensor data may include location data indicating that a user of the personal monitoring device 102 has entered an area, exited an area, is within a certain distance of a location, is outside of a certain distance from a location, and the like. In other implementations, the sensor data may include environmental data indicating that user is within an environment in which one or more conditions (e.g., temperature, air quality, etc.) is over a threshold, below a threshold, or otherwise outside of a particular range. In still other implementations, the sensor data may indicate that movement of the user of the personal monitoring device 102 exceeds a predetermined limit (e.g., high acceleration or deceleration in response to a fall or collision).

More generally, the server system 104 may generate and transmit an alert to the personal monitoring device 102, one or more remote computing devices (such as the remote computing device 106), or take other alert actions in response to a predetermined condition being met. In certain implementations, at least some of the conditions for which alerts are generated may be universally applied to all personal monitoring devices. However, at least some conditions may also be dynamically generated and/or specifically tailored to each user of a personal monitoring device. Accordingly, the server system may store information that includes particular alert conditions for each personal monitoring device user and respective actions to be taken in the event an alert condition is met. Among other things, such actions may include generating and transmitting alerts to the personal monitoring device, generating and transmitting messages to reconfigure the personal monitoring device, generating and transmitting alerts to the personal monitoring device, contacting emergency services, and the like. For purposes of the present disclosure, the information defining the conditions under which actions are to be taken by the server system for a personal monitoring device and the particular actions to be taken by the server system when such conditions are met are generally referred to as a user profile. Each condition and action combination included in a given user profile is referred to herein as a user profile entry. It should be noted, however, that the user profile may be generated, formatted, and structured in any suitable way, provided the information contained within the user profile may be used to determine when sensor data received from the personal monitoring device indicates an alert is to be generated and transmitted. Once generated, each user profile may be stored in the server system 104 or in a data store 118 accessible by the server system 104.

A given user profile may include multiple entries corresponding to a particular metric. For example, a user profile may have entries covering increasing levels of a pollutant, with each entry including a corresponding level of action to be taken. As another example, different actions may be initiated in response to the personal monitoring device measuring different levels of acceleration. So, a simple text message may be generated in response to a first level of acceleration measured by the personal monitoring device indicating a light contact or collision, but an emergency service may immediately contacted in response to a second level of acceleration indicative of a severe fall or similar traumatic event.

User profiles in accordance with the present disclosure may be generated in various ways. For example, in certain implementations, a user of the remote computing device 106 may log onto a web-based portal, app, or similar interface hosted by the server system 104 and add entries to a user profile for a particular personal monitoring device, each entry specifying one or more conditions and one or more actions to be taken when the one or more conditions are met. For example and without limitation, in the case of environmental data, the user of the remote computing device 106 may specify particular values or ranges for air quality metrics, temperature, and the like and identify recipients of alerts or calls when the values or ranges are met. In the case of location data, the user of the remote computing device 106 may define geographic areas or geographic boundaries and actions to be taken when a user of the personal monitoring device 102 exits/enters the identified areas or crosses the geographic boundaries. In other implementations, the user of the remote computing device 106 may identify a location or landmark and specify a radius from the location or landmark. An alert may then be generated when the user of the personal monitoring device 102 crosses the radius. In still other implementations, the user of the remote computing device 106 may select particular classes of geographic features (e.g., bodies of water, highways, industrial facilities, types of stores, etc.) and a radius or distance within which an alert will be generated.

In certain implementations, a user profile may be based, in part, on data, such as health and safety standards, medical recommendations, or geographic data, provided by a third-party. For example, the user profile may include conditions and actions related to environmental exposure levels as determined by an environmental agency, health and safety organization, or other similar entity that provides data regarding exposure limits and safety. Similarly, map data may be used to identify potentially hazardous geographic features, landmarks, or locations from which user profile entries may be generated. Third party data used to generate user profile entries may also include user profiles or data collected from other personal monitoring devices. For example, the user profile for a user of a first personal monitoring device may be used to generate a user profile for a user of a second personal monitoring device having similar characteristics (e.g., age, medical conditions, etc.).

iii. Clinical Trial Data Collection

Personal monitoring devices described herein may be used to provide improved data collection and environmental exposure information during clinical trials. For example, participants in a trial for a drug or medical device may each be provided with a personal monitoring device such that environmental exposure, activity, and location information may be collected for each participant. Such information may be collected from each personal monitoring device by a server system and subsequently included in the clinical data for the trial. Doing so may more effectively determine the efficacy of the drug, device, or treatment being tested and may provide additional insights regarding potential effects related to environmental exposure, personal activity, and the like. Although applications including environmental monitoring may be particularly useful for trials related to respiratory-related conditions, the personal monitoring devices may be used more broadly in any application in which the location, environmental exposure, movement patterns, or other similar data for a participant may be a factor in the efficacy of a particular treatment.

iv. Family Supervision

As previously discussed, certain applications of the present disclosure may be related to monitoring and supervision of family members or similar individuals. For example, a parent may provide a personal monitoring device to a child and configure the personal monitoring device (e.g., using the remote computing device 106 of FIG. 1) to provide warnings or alerts to the parent based on the conditions measured by the personal monitoring device. For example, the parent may configure the personal monitoring device to provide warnings or alerts based on, among other things, the location of the child, environmental conditions around the child, and the like. In certain implementations, parents may also be able to send text, voice, video, or other messages to the personal monitoring device for display on the device's screen or playback using an audio output of the personal monitoring device.

v. Traffic Flow Monitoring

As noted, personal monitoring devices in accordance with the present disclosure generally include location-based sensors, such as GPS units, as movement sensors, such as accelerometers. To the extent a user of the personal monitoring device has the device while travelling in a vehicle, the GPS and accelerometer information collected by the personal monitoring device may be provided to a server (e.g., server system 104 of FIG. 1) or a similar computing system for purposes of analyzing traffic flow patterns and/or similar travel information. For example and without limitation, such information may be used to determine approximate travel times between locations.

vi. Device Location and Tethering

In certain applications, a user of the personal monitoring device may assign/associate the personal monitoring device to one or more remote computing devices, such as smart phones or tablets. Once associated, the distance between the two devices may be monitored. In certain implementations, such monitoring may include determining the location of each device and calculating a distance between the two. Alternatively or in addition to calculating a distance between the devices, the association between the devices may include establishing a communication link (such as a Bluetooth link) between the devices.

Once the personal monitoring device is associated with a remote computing device, the personal monitoring device may be virtually "tethered" to the remote computing device. Once tethered, alerts or warning may be issued to either device in response to a distance between the devices being exceeded. In implementations in which the distance between the devices is calculated, for example, an alert or warning may be issued to either device when the distance exceeds a preconfigured distance (e.g., 100 yards, 500 yards, etc.). Similarly, when the devices are tethered by a communication link, an alert or warning may be issued when the communication link is broken, e.g., by exceeding the range of the communication link.

The foregoing techniques have various applications. For example, a user may tether their personal monitoring device to their mobile phone to facilitate tracking of their devices. More specifically, by tethering their mobile device with their personal monitoring device, the user may be alerted if they leave a location with only their personal monitoring device or only their mobile device and leave the other device behind.

In another example, a parent may tether their mobile phone to personal monitoring devices for each of their children. Each of the parent and the child may then receive warnings or alerts when the tether is broken or exceeds a particular distance. In certain implementations, the parent may be able to configure different tethers for each child. For example, older children may be given a longer tether while younger children may be given a shorter tether. Similarly, different warning and alert severities may be assigned to different distances. So, for example, a gentle buzzing or audible alert may be issued when a child exceeds a first distance from the parent, but a call between the remote computing device of the parent and the personal monitoring device of the child may be initiated if the child exceeds a second distance from the parent.

vii. Exercise and Fitness Tracking

Accelerometer, GPS, and other similar data generated by the personal monitoring device may also be used to provide exercise and fitness tracking functionality for the user of the personal monitoring device. Among other things, the personal monitoring device may measure and provide fitness-related metrics such as a step count or a distance travelled over a given time period. In certain implementations, the personal monitoring device may also be configured to pair with and receive data from one or more biometric or fitness-related sensors, such as a heart rate monitor, smart watch, or additional fitness tracking device and to provide such data to the server system for additional processing.

viii. Panic Button/Preset Number

As noted above in the example devices of FIGS. 4-7C, the personal monitoring device may include panic button or similar functionality that automatically contacts a specified recipient. For example, the personal monitoring device may include a button (either physical or virtual) that, when pressed, automatically transmits a message or attempts to connect with the recipient. In certain implementations, the personal monitoring device may use a cellular chip to contact 911 or similar emergency services. Once connected, the personal monitoring device may allow for two-way voice communication. Although emergency services are envisioned as one possible recipient contacted in response to activation of the panic button, it should be appreciated that any suitable recipient (such as a caretaker, parent, medical professional, or other individual) may be contacted in response to activation of the panic button.

ix. Fall/Crash Alert and Related Functionality

The personal monitoring device may be configured to automatically perform certain functions, such as contacting particular individuals or emergency services, in response to an accelerometer of the device measuring acceleration that exceeds certain thresholds and indicates a fall, crash, or other potentially traumatic event. More specifically, the personal monitoring device may be programmed with movement thresholds corresponding to a user falling, being in an automobile accident, or other similar events. When such events are detected, the personal monitoring device may call or send a message to a predetermined contact, which may include 911 or other emergency services.

The foregoing functionality may also be performed, at least in part, by the server system to which the personal monitoring device provides sensor data. For example, in certain implementations, the personal monitoring device may be configured to automatically transmit a message to the server system when an acceleration threshold is exceeded. In response, the server system may take various actions including such as issuing a corresponding alert or warning to remote computing devices associated with the personal monitoring device. Such alerts or warnings may include the location of the event and other similar information. Alternatively, the server system may facilitate opening a line of communication between the personal monitoring device and the remote computing device, such as by initiating a phone call or text message exchange between the devices.

In still other implementations, the server system may automatically transmit various messages to the personal monitoring device in response to being notified of a potential fall or crash. In a first example, the server system may automatically generate and transmit a message requesting current location data (or any other sensor data) from the personal monitoring device. In another example, the server system may automatically generate and transmit a reconfiguration message that causes the personal monitoring device to increase the frequency at which the personal monitoring device provides sensor data such as, but not limited to, location data.

x. Integration with Smart Devices

The personal monitoring device may be configured to pair with, communicate with, and/or control various smart devices. Such smart devices may include, without limitation, smart lighting systems, appliances, security systems, digital assistants, and the like. In one specific implementation, the personal monitoring device may be used as an input device for such other smart devices. In such implementations, the personal monitoring device may receive inputs from the user (including, without limitation, button presses, touchscreen inputs, and voice commands) and transmit such inputs to the other smart devices. The personal monitoring device may also be configured to receive messages from such devices, which may then be displayed on the display of the personal monitoring device.

xi. Payment Features

The personal monitoring device may include functionality for facilitating payments. For example, credit card or other payment information may be stored in the personal monitoring device. The personal monitoring device may then be able to wirelessly connect to and communicate with point-of-sale or payment terminals to facilitate payment for goods and services.

xii. Weather/Environmental Station

While described herein as primarily a mobile and wearable personal monitoring device, it should be appreciated that the personal monitoring device may also be configured to be operated as a weather or environmental station that collects and provides environmental and weather data. Such data may be collected, for example, using temperature, air quality, or other environment-related sensors of the personal monitoring device and provided to the server system for further processing or provision to one or more weather-related external computer systems.

xiii. Identifying Mode of Transportation

Personal monitoring devices according to the present disclosure may provide each of location data (e.g., GPS data) and movement data (e.g., accelerometer data) to a server system. In addition to identify the location of personal monitoring devices and the occurrence of certain events (e.g., falls, entering and exiting geographic areas, changes in environ mental conditions, etc.), the server system may use information received from the personal monitoring device to identify a mode of transportation associated with the personal monitoring device. Identifying a mode of transportation may be useful, for example, in determining whether a user of the personal is involved in an accident while in a car, riding a bike, or on foot such that appropriate emergency services may be contacted and an alert with a suitable severity may be transmitted to caregivers or other individuals associated with the user.

To identify a mode of transportation, data corresponding to the user's location and acceleration may be received by the server from the personal monitoring device of the user. Based on the location data, the server may determine the user's speed, which may be used to narrow possible modes of transportation. For example, if the location data indicates that the user is travelling at speeds in excess of 20 miles/hour, the server may assume that the user is cycling, in a car, or using some form of vehicle. Location data may also be used to narrow possible modes of transportation based on the user's location. For example, if a user's location indicates that they are on a freeway, it is likely that the user is in a vehicle. Similarly, if a user is located in a park or similar area with only limited roads, the server may assume the user is more likely on foot or using a lower speed vehicle, such as a bicycle.

In addition to location data, the server may analyze acceleration data to further determine the user's mode of transportation. For example, in an urban setting, a user's speed and location may be similar whether they are in an automobile or riding a bicycle and, as a result, speed and location may be insufficient to clearly determine the user's mode of transportation. In such situations, the server may further consider acceleration data (e.g., as collected using an accelerometer incorporated into devices of the present disclosure) to facilitate further distinction. For example and without limitation, at least certain distinctions may be made by the server based on the user's average acceleration over a certain time period, with larger vehicles generally exhibiting slower acceleration than smaller vehicles. Alternatively, the server may examine an acceleration profile of the user to determine the mode of transportation. Such examination may include comparing the user's acceleration to templates, curves, or similar data associated with different modes of transportation and stored at the server.

In certain implementations, mode of transportation information may be used to subsequently identify potentially hazardous conditions and to generate corresponding alerts. For example, data received from a personal monitoring device may indicate that a user of the device was travelling in a car that was subsequently parked. Subsequently, temperature data from the personal monitoring device may be collected and monitored to determine if conditions within the car (e.g., heat) exceed safe levels and, if so, a corresponding alert may be issued to a caregiver, emergency services, etc.

xiv. Deviation from Routine Activity

Implementations of the present disclosure may also include functionality for monitoring deviations from routine activity. For example, sensor data collected from a personal monitoring device of a user may be processed by the server system to generate a behavioral profile for the user. The behavioral profile may include, among other things, travel patterns and times for the user (e.g., commutes, routes to/from school). The behavioral profile may also include location and time information corresponding to common locations for the user at different times of the day. So, for example, the behavioral profile may specify that a user of a personal monitoring device is generally within a certain radius of a school or similar building from around 8:00 am to around 3:00 pm on typical weekdays.

To the extent sensor data received from the personal monitoring device indicates a deviation from a behavioral profile of a user, an alert may be generated and transmitted to a caretaker or other individual. For example, if a child deviates from their typical route to or from school or leaves school during normal hours, an alert may be generated and transmitted to a parent. Alerts may also be generated if aspects of the user's behavior other than route or location change. For example, an alert may be generated if the sensor data indicates that a child has entered a vehicle when the child normally walks or rides a bike, regardless of the route taken.

G. Example Computing System

Figure 13:
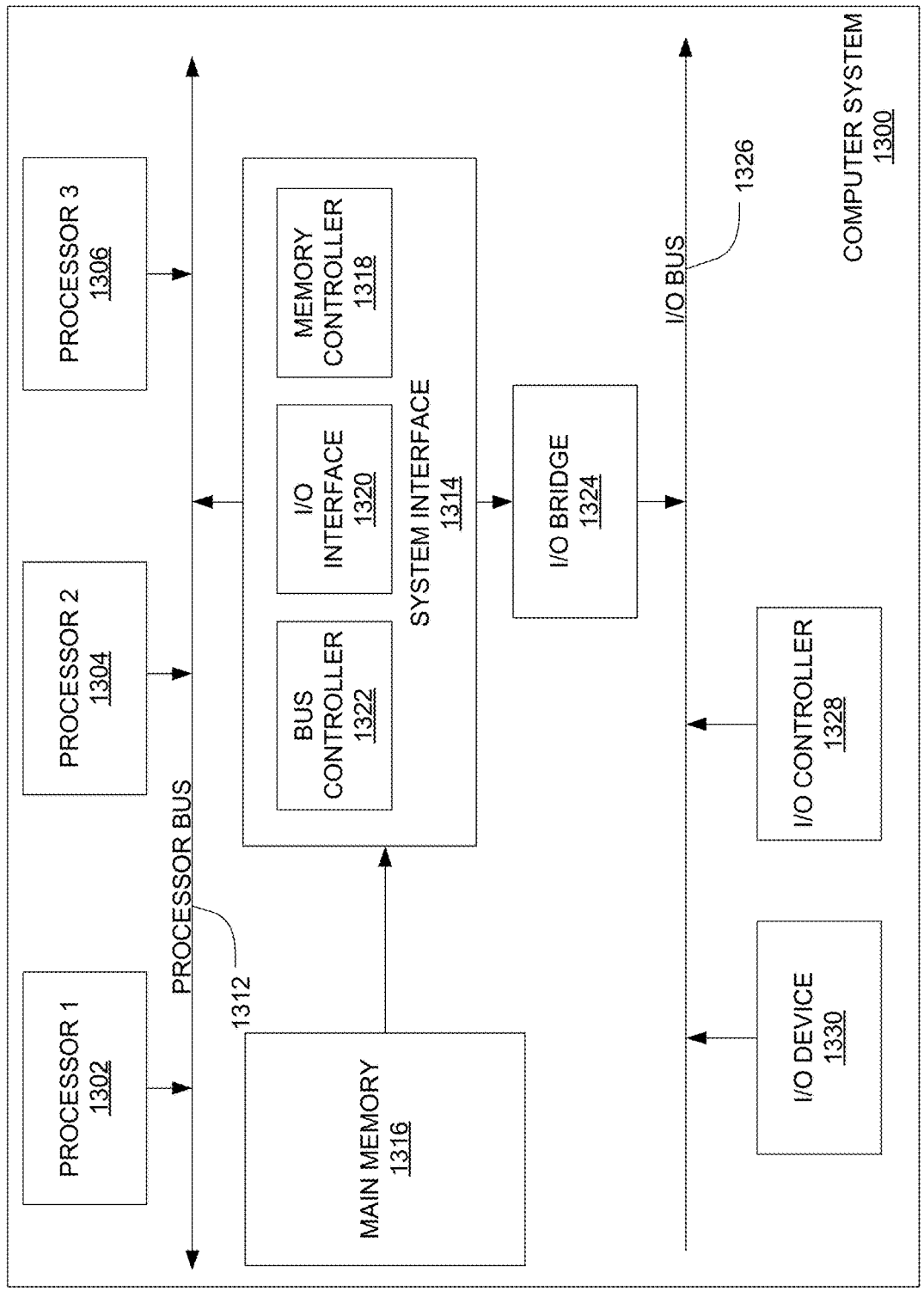
FIG. 13 is a block diagram of a computing system that may be used to implement aspects of the present disclosure.

FIG. 13 is a block diagram illustrating an example of a computing device or computer system 1300 which may be used in implementing the embodiments of the systems and methods disclosed above. In particular, the computing device of FIG. 13 is one embodiment of the server system 104 or the remote computing device 106 illustrated in FIG. 1 or a computing device that otherwise performs one of more of the operations described above. The computer system (system) includes one or more hardware processors 1302-1306. Processors 1302-1306 may include one or more internal levels of cache (not shown) and a bus controller 1322 or bus interface unit to direct interaction with the processor bus 1312. Processor bus 1312, also known as the host bus or the front side bus, may be used to couple the processors 1302-1306 with the system interface 1314. System interface 1314 may be connected to the processor bus 1312 to interface other components of the system 1300 with the processor bus 1312. For example, system interface 1314 may include a memory controller 1318 for interfacing a main memory 1316 with the processor bus 1312. The main memory 1316 typically includes one or more memory cards and a control circuit (not shown). System interface 1314 may also include an input/output (I/O) interface 1320 to interface one or more I/O bridges (e.g. I/O bridge 1324) or I/O devices with the processor bus 1312. One or more I/O controllers and/or I/O devices may be connected with the I/O bus 1326, such as I/O controller 1328 and I/O device 1330, as illustrated.

I/O device 1330 may also include an input device (not shown), such as an alphanumeric input device, including alphanumeric and other keys for communicating information and/or command selections to the processors 1302-1306. Another type of user input device includes cursor control, such as a mouse, a trackball, or cursor direction keys for communicating direction information and command selections to the processors 1302-1306 and for controlling cursor movement on the display device.

System 1300 may include a dynamic storage device, referred to as main memory 1316, or a random access memory (RAM) or other computer-readable devices coupled to the processor bus 1312 for storing information and instructions to be executed by the processors 1302-1306. Main memory 1316 also may be used for storing temporary variables or other intermediate information during execution of instructions by the processors 1302-1306. System 1300 may include a read only memory (ROM) and/or other static storage device coupled to the processor bus 1312 for storing static information and instructions for the processors 1302-1306. The system set forth in FIG. 13 is but one possible example of a computer system that may employ or be configured in accordance with aspects of the present disclosure.

According to one embodiment, at least some of the above methods and techniques described herein may be performed by computer system 1300 in response to processor 1304 executing one or more sequences of one or more machine-readable instructions contained in main memory 1316. These instructions may be read into main memory 1316 from another machine-readable medium, such as a storage device. Execution of the sequences of instructions contained in main memory 1316 may cause processors 1302-1306 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 1316. Common forms of machine-readable media may include, but are not limited to, magnetic storage media; optical storage media; magneto-optical storage media; read only memory (ROM); random access memory (RAM); erasable programmable memory (e.g., EPROM and EEPROM); flash memory; or other types of media suitable for storing electronic instructions.

Embodiments of the present disclosure include various operations, which are described in this specification. The operations may be performed by hardware components or may be embodied in machine-executable instructions, which may be used to cause a general-purpose or special-purpose processor programmed with the instructions to perform the operations. Alternatively, the operations may be performed by a combination of hardware, software, and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

What is claimed is:

1. A method of tracking computing devices comprising:
at a first computing device:
receiving first sensor data from a second computing device at a first rate, the first sensor data from a sensor of a plurality of sensors of the second computing device, each sensor of the plurality of sensors associated with a respective identifier;
determining that the first sensor data indicates a reconfiguration condition;
responsive to determining the first sensor data indicates the reconfiguration condition, transmitting a reconfiguration message to the second computing device, the reconfiguration message including the identifier associated with the sensor and a value corresponding to a second rate, wherein, when received by the second computing device, the reconfiguration message causes the second computing device to begin providing sensor data from the sensor to the first computing device at the second rate;
receiving, from a third computing device different than the second computing device, a first request for second sensor data obtainable from the second computing device;
responsive to receiving the first request, transmitting a second request for the second sensor data to the second computing device;
subsequent to transmitting the second request for the second sensor data, receiving the requested sensor data from the second computing device; and
transmitting the requested sensor data from the first computing device to the third computing device.

2. The method of claim 1, wherein the first sensor data includes a location of the second computing device and the reconfiguration condition includes the second computing device crossing a geographic boundary.

3. The method of claim 1, wherein the first sensor data includes acceleration of the second computing device and the reconfiguration condition includes an acceleration threshold.

4. The method of claim 1, wherein the first sensor data includes an environmental metric and the reconfiguration condition includes a limit for the environmental metric.

5. The method of claim 4, wherein the environmental metric includes at least one of an air quality metric and temperature.

6. The method of claim 1 further comprising, at the first computing device:
receiving a location of the second computing device; and
in response to determining the sensor data indicates the reconfiguration condition, transmitting the location of the second computing device to a computing device different than the second computing device.

7. The method of claim 1, further comprising, at the first computing device:
receiving a low power notification from the second computing device; and
responsive to receiving the low power notification, transmitting a request for sensor data to the second computing device.

8. A method of tracking computing devices comprising:
at a first computing device:
periodically transmitting sensor data at a first rate from to a second computing device, the sensor data corresponding to a sensor of a plurality of sensors of the first computing device;
receiving a reconfiguration message from the second computing device, the reconfiguration message including an identifier assigned to the sensor and a value corresponding to a second rate different from the first rate;
responsive to receiving the reconfiguration message, periodically transmitting the sensor data at the second rate;
responsive to a low power condition of the first computing device, each of transmitting a low power notification to the second computing device and stopping periodic transmission of the sensor data;
subsequent to stopping periodic transmission of sensor data, receiving a sensor data request from the second computing device; and
responsive to receiving the sensor data request, transmitting the sensor data to the second computing device.

9. The method of claim 8, wherein the sensor data includes a location of the first computing device and the reconfiguration condition includes the second computing device crossing a geographic boundary.

10. The method of claim 8, wherein the sensor data includes acceleration of the first computing device and the reconfiguration condition includes an acceleration threshold.

11. The method of claim 8, wherein the sensor data includes an environmental metric and the reconfiguration condition includes a limit for the environmental metric.

12. The method of claim 8 further comprising, at the first computing device:
responsive to receiving a request from the second computing device for requested sensor data obtainable from the first computing device, transmitting the requested sensor data to the second computing device.

13. A system for tracking computing devices, the system comprising:
a first computing device comprising one or more processors and one or more memories storing machine readable instructions that, when executed by the one or more processors, cause the one or more processors to:
receive first sensor data from a second computing device at a first rate, the first sensor data from a sensor of a plurality of sensors of the second computing device, each sensor of the plurality of sensors associated with a respective identifier;
determine that the first sensor data indicates a reconfiguration condition;
responsive to determining the first sensor data indicates the reconfiguration condition, transmit a reconfiguration message to the second computing device, the reconfiguration message including the identifier associated with the sensor and a value corresponding to a second rate, wherein, when received by the second computing device, the reconfiguration message causes the second computing device to begin providing sensor data from the sensor to the first computing device at the second rate;
receive, from a third computing device different than the second computing device, a first request for second sensor data obtainable from the second computing device;
responsive to receiving the first request, transmit a second request for the second sensor data to the second computing device;
subsequent to transmitting the second request for the second sensor data, receive the requested sensor data from the second computing device; and
transmit the requested sensor data from the first computing device to the third computing device.

14. The system of claim 13, wherein the sensor data includes at least one of a location of the second computing device and the reconfiguration condition includes the second computing device crossing a geographic boundary.

15. The system of claim 13, wherein the sensor data includes acceleration of the second computing device and the reconfiguration condition includes an acceleration threshold.

16. The system of claim 13, wherein the sensor data includes an environmental metric and the reconfiguration condition includes a limit for the environmental metric.

17. The system of claim 13, wherein the instructions further cause the one or more processors to:
receive a low power notification from the second computing device; and
responsive to receiving the low power notification, transmit a request for sensor data to the second computing device.

18. A system for tracking computing devices, the system comprising:
a first computing device comprising one or more processors and one or more memories storing machine readable instructions that, when executed by the one or more processors, cause the one or more processors to:
periodically transmit sensor data at a first rate from to a second computing device, the sensor data corresponding to a sensor of a plurality of sensors of the first computing device;
receive a reconfiguration message from the second computing device, the reconfiguration message including an identifier assigned to the sensor and a value corresponding to a second rate different from the first rate;

responsive to receiving the reconfiguration message, periodically transmitting the sensor data at the second rate;

responsive to a low power condition of the first computing device, each of transmitting a low power notification to the second computing device and stopping periodic transmission of sensor data;

subsequent to stopping periodic transmission of sensor data, receiving a sensor data request from the second computing device; and responsive to receiving the sensor data request, transmitting sensor data to the second computing device.

19. The system of claim 13, wherein the sensor data includes at least one of a location of the first computing device, an acceleration of the first computing device, and an environmental metric.

20. The system of claim 13, wherein the instructions further cause the one or more processors to:

receive a request from the second computing device for requested sensor data obtainable from the first computing device; and transmit the requested sensor data to the second computing device.

* * * * *